US012763210B2

(12) United States Patent
Ji et al.

(10) Patent No.: US 12,763,210 B2
(45) Date of Patent: Oct. 13, 2026

(54) METHOD AND DIAGNOSTIC APPARATUS FOR DETERMINING ENTERIC DISORDER USING MACHINE LEARNING MODEL

(71) Applicant: HEM PHARMA INC., Pohang-si (KR)

(72) Inventors: Yo Sep Ji, Suwon-si (KR); So Young Park, Suwon-si (KR)

(73) Assignee: HEM PHARMA INC., Pohang-si (KR)

( * ) Notice: Subject to any disclaimer, the term of this patent is extended or adjusted under 35 U.S.C. 154(b) by 88 days.

(21) Appl. No.: 18/518,698

(22) Filed: Nov. 24, 2023

(65) Prior Publication Data

US 2024/0096496 A1 Mar. 21, 2024

Related U.S. Application Data

(63) Continuation of application No. PCT/KR2022/007419, filed on May 25, 2022.

(30) Foreign Application Priority Data

May 25, 2021 (KR) ........................ 10-2021-0066616

(51) Int. Cl.
*G16H 50/20* (2018.01)
*G16B 5/00* (2019.01)
*G16B 40/20* (2019.01)

(52) U.S. Cl.
CPC ............... *G16H 50/20* (2018.01); *G16B 5/00* (2019.02); *G16B 40/20* (2019.02)

(58) Field of Classification Search
None
See application file for complete search history.

(56) References Cited

U.S. PATENT DOCUMENTS

| | | | | |
|---|---|---|---|---|
| 10,346,588 B2 | 7/2019 | Apte et al. | | |
| 2014/0179726 A1* | 6/2014 | Bajaj | .................... | A61K 31/437 435/6.12 |

(Continued)

FOREIGN PATENT DOCUMENTS

| | | | |
|---|---|---|---|
| KR | 102057047 | B1 | 12/2019 |
| KR | 10-2020-0054203 | A | 5/2020 |
| KR | 10-2020-0090135 | A | 7/2020 |
| KR | 10-2021-0027058 | A | 3/2021 |

(Continued)

OTHER PUBLICATIONS

B. Wingfield, S. Coleman, T. M. McGinnity and A. J. Bjourson, "A metagenomic hybrid classifier for paediatric inflammatory bowel disease," 2016 International Joint Conference on Neural Networks (IJCNN), Vancouver, BC, Canada, 2016, pp. 1083-1089, doi: 10.1109/IJCNN.2016.7727318. (Year: 2016).*

(Continued)

*Primary Examiner* — Devin C Hein
*Assistant Examiner* — Vincent C Ilagan
(74) *Attorney, Agent, or Firm* — NKL LAW; Jae Youn Kim

(57) ABSTRACT

A method for determining an enteric disorder by using a machine learning model, including: analyzing a mixture of a sample collected from a subject and a gut environment-like composition; extracting multiple microbial data based on an analysis result of the mixture; selecting a microbe-related feature to be used for the machine learning model from the multiple microbial data based on a predetermined feature selection algorithm; training the machine learning model by using the microbe-related feature; and determining an enteric disorder by inputting, into the trained machine learning model, the microbial data collected from a subject to be tested.

4 Claims, 28 Drawing Sheets

(56) References Cited

U.S. PATENT DOCUMENTS

| | | | | |
|---|---|---|---|---|
| 2017/0199189 | A1* | 7/2017 | Wade | G16H 50/30 |
| 2017/0286620 | A1 | 10/2017 | Apte et al. | |
| 2021/0063407 | A1* | 3/2021 | Park | A61P 1/00 |
| 2021/0128644 | A1* | 5/2021 | Kashyap | A61K 35/741 |
| 2022/0328132 | A1* | 10/2022 | Kubinski | G16H 10/40 |

FOREIGN PATENT DOCUMENTS

| | | |
|---|---|---|
| KR | 102241357 A | 4/2021 |
| KR | 10-2373886 B1 | 3/2022 |

OTHER PUBLICATIONS

Wingfield, B.et al., "A metagenomic hybrid classifier for paediatric inflammatory bowel disease," 2016 International Joint Conference on Neural Networks (IJCNN), Vancouver, BC, Canada, 2016, pp. 1083-1089, doi: 10.1109/IJCNN.2016.7727318. (Year : 2016).*

Ma, X. et al., "Study of the Gastrointestinal Heat Retention Syndrome in Children: From Diagnostic Model to Biological Basis," Evidence-Based Complementary and Alternative Medicine, 2019, 5303869, 12 pages, 2019. https://doi.org/10.1155/2019/5303869 (Year: 2019).*

Townes, F.W., et al. "Feature selection and dimension reduction for single-cell RNA-Seq based on a multinomial model," Genome Biol 20, 295 (2019). https://doi.org/10.1186/s13059-019-1861-6 (Year: 2019).*

Wingfield, B. et al., 2016 International Joint Conference on Neural Networks (IJCNN), Vancouver, BC, Canada, 2016, pp. 1083-1089, doi: 10.1109/IJCNN.2016.7727318. (Year: 2016).*

International Search Report of PCT/KR2022/007419 dated Sep. 1, 2022.

* cited by examiner

(a) EXAMPLE

1 ~ 23 features (b) COMPARATIVE EXAMPLE

15 ~ 20 features (a) EXAMPLE 14 features

(b) COMPARATIVE EXAMPLE

20 features

FIG. 6C

(a) EXAMPLE

```
> clinic.pmas.entericdisorder.xgb.imp.mtx
```

| | Feature | Gain | Cover | Frequency |
|---|---|---|---|---|
| 1: | Clostridiaceae_Clostridium_sensu_stricto_1_uncultured_bacterium | 0.18888725 | 0.165778181 | 0.1464968153 |
| 2: | Bifidobacteriaceae_Bifidobacterium_NA | 0.18082699 | 0.183758211 | 0.1847133758 |
| 3: | Tannerellaceae_Parabacteroides_Parabacteroides_sp. | 0.13468806 | 0.159262241 | 0.1537761601 |
| 4: | Bacteroidaceae_Bacteroides_NA | 0.09719670 | 0.075700854 | 0.0891719745 |
| 5: | Lachnospiraceae_.Ruminococcus._gauvreauii_group_NA | 0.09477575 | 0.079178110 | 0.0873521383 |
| 6: | Ruminococcaceae_Subdoligranulum_NA | 0.09079375 | 0.122907679 | 0.1301182894 |
| 7: | Erysipelatoclostridiaceae_Erysipelatoclostridium_Erysipelatoclostridium_ramosum | 0.05629341 | 0.059837047 | 0.0536851683 |
| 8: | UCG.010_UCG.010_NA | 0.03271328 | 0.013119431 | 0.0090991811 |
| 9: | Lachnospiraceae_GCA.900066575_uncultured_bacterium | 0.02974374 | 0.024672987 | 0.0172884440 |
| 10: | Veillonellaceae_Veillonella_NA | 0.02895315 | 0.028434277 | 0.0309372157 |
| 11: | Ruminococcaceae_.Eubacterium._siraeum_group_.Eubacterium._siraeum | 0.02367565 | 0.020039034 | 0.0218380346 |
| 12: | Bacteroidaceae_Bacteroides_Bacteroidaceae_bacterium | 0.01656618 | 0.017485964 | 0.0191082803 |
| 13: | RF39_RF39_gut_metagenome | 0.01266009 | 0.045282763 | 0.0527752502 |
| 14: | Erysipelatoclostridiaceae_Coprobacillus_uncultured_bacterium | 0.01129567 | 0.001681599 | 0.0009099181 |

FIG. 6D

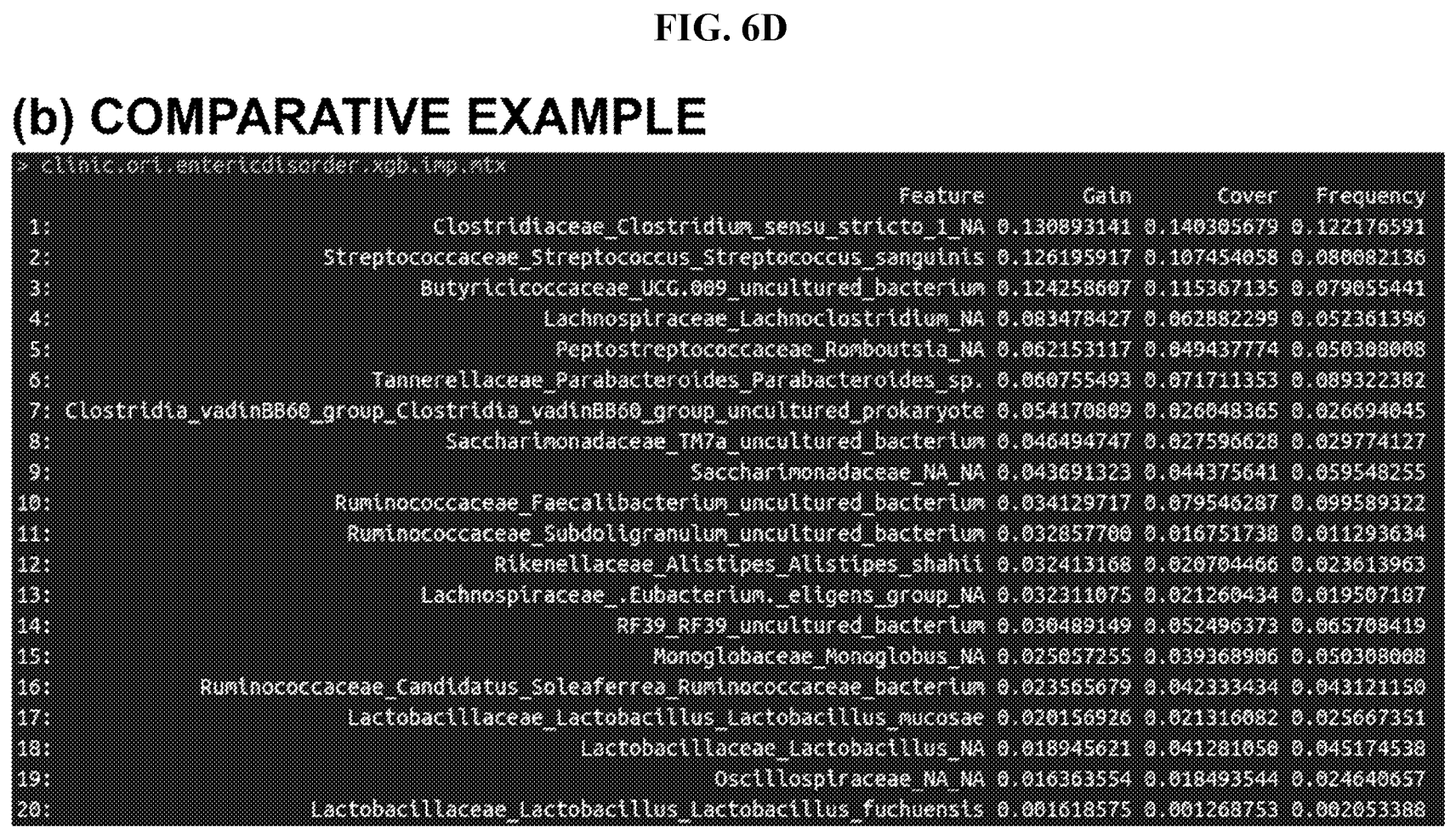

(b) COMPARATIVE EXAMPLE

> clinic.ori.entericdisorder.xgb.imp.mtx

| | Feature | Gain | Cover | Frequency |
|---|---|---|---|---|
| 1: | Clostridiaceae_Clostridium_sensu_stricto_1_NA | 0.130893141 | 0.140305679 | 0.122176591 |
| 2: | Streptococcaceae_Streptococcus_Streptococcus_sanguinis | 0.126195917 | 0.107454058 | 0.080082136 |
| 3: | Butyricicoccaceae_UCG.009_uncultured_bacterium | 0.124258607 | 0.115367135 | 0.079055441 |
| 4: | Lachnospiraceae_Lachnoclostridium_NA | 0.083478427 | 0.062882299 | 0.052361396 |
| 5: | Peptostreptococcaceae_Romboutsia_NA | 0.062153117 | 0.049437774 | 0.050308008 |
| 6: | Tannerellaceae_Parabacteroides_Parabacteroides_sp. | 0.060755493 | 0.071711353 | 0.089322382 |
| 7: | Clostridia_vadinBB60_group_Clostridia_vadinBB60_group_uncultured_prokaryote | 0.054170809 | 0.026048365 | 0.026694045 |
| 8: | Saccharimonadaceae_TM7a_uncultured_bacterium | 0.046494747 | 0.027596628 | 0.029774127 |
| 9: | Saccharimonadaceae_NA_NA | 0.043691323 | 0.044375641 | 0.059548255 |
| 10: | Ruminococcaceae_Faecalibacterium_uncultured_bacterium | 0.034129717 | 0.079546287 | 0.099589322 |
| 11: | Ruminococcaceae_Subdoligranulum_uncultured_bacterium | 0.032857700 | 0.016751738 | 0.011293634 |
| 12: | Rikenellaceae_Alistipes_Alistipes_shahii | 0.032413168 | 0.020704466 | 0.023613963 |
| 13: | Lachnospiraceae_.Eubacterium._eligens_group_NA | 0.032311075 | 0.021260434 | 0.019507187 |
| 14: | RF39_RF39_uncultured_bacterium | 0.030489149 | 0.052496373 | 0.065708419 |
| 15: | Monoglobaceae_Monoglobus_NA | 0.025057255 | 0.039368906 | 0.050308008 |
| 16: | Ruminococcaceae_Candidatus_Soleaferrea_Ruminococcaceae_bacterium | 0.023565679 | 0.042333434 | 0.043121150 |
| 17: | Lactobacillaceae_Lactobacillus_Lactobacillus_mucosae | 0.020156926 | 0.021316082 | 0.025667351 |
| 18: | Lactobacillaceae_Lactobacillus_NA | 0.018945621 | 0.041281050 | 0.045174538 |
| 19: | Oscillospiraceae_NA_NA | 0.016363554 | 0.018493544 | 0.024640657 |
| 20: | Lactobacillaceae_Lactobacillus_Lactobacillus_fuchuensis | 0.001618575 | 0.001268753 | 0.002053388 |

(A) PCoA plot (Unweighted UniFrac Distance)

Distances in PCoA plot (Total 8 samples)
Mann Whitney test (P value : 0.0013)

(B) Unweighted UniFrac Distance

Unweighted UniFrac Distance

FIG. 8B

```
Permutation test for adonis under reduced model
Terms added sequentially (first to last)
Permutation: free
Number of permutations: 999

adonis2(formula = physeq.asv_UWunif ~ MODvar, data = sampledf)
         Df SumOfSqs     R2      F Pr(>F)
MODvar    1  0.20922 0.2296 4.1724  0.001 ***
Residual 14  0.70202 0.7704
Total    15  0.91124 1.0000
---
Signif. codes:  0 '***' 0.001 '**' 0.01 '*' 0.05 '.' 0.1 ' ' 1
```

```
        Homogeneity of multivariate dispersions

Call: betadisper(d = physeq.asv_UWunif, group = sampledf$MODvar)

No. of Positive Eigenvalues: 15
No. of Negative Eigenvalues: 0

Average distance to median:
 MCMOD   SMOD
0.1792 0.2340

Eigenvalues for PCoA axes:
(Showing 8 of 15 eigenvalues)
  PCoA1   PCoA2   PCoA3   PCoA4   PCoA5   PCoA6   PCoA7   PCoA8
0.24326 0.12593 0.08415 0.07367 0.06846 0.05442 0.04798 0.04487
```

(a) EXAMPLE

AUC: 0.9653

(b) COMPARATIVE EXAMPLE
AUC: 0.8400

FIG. 10A

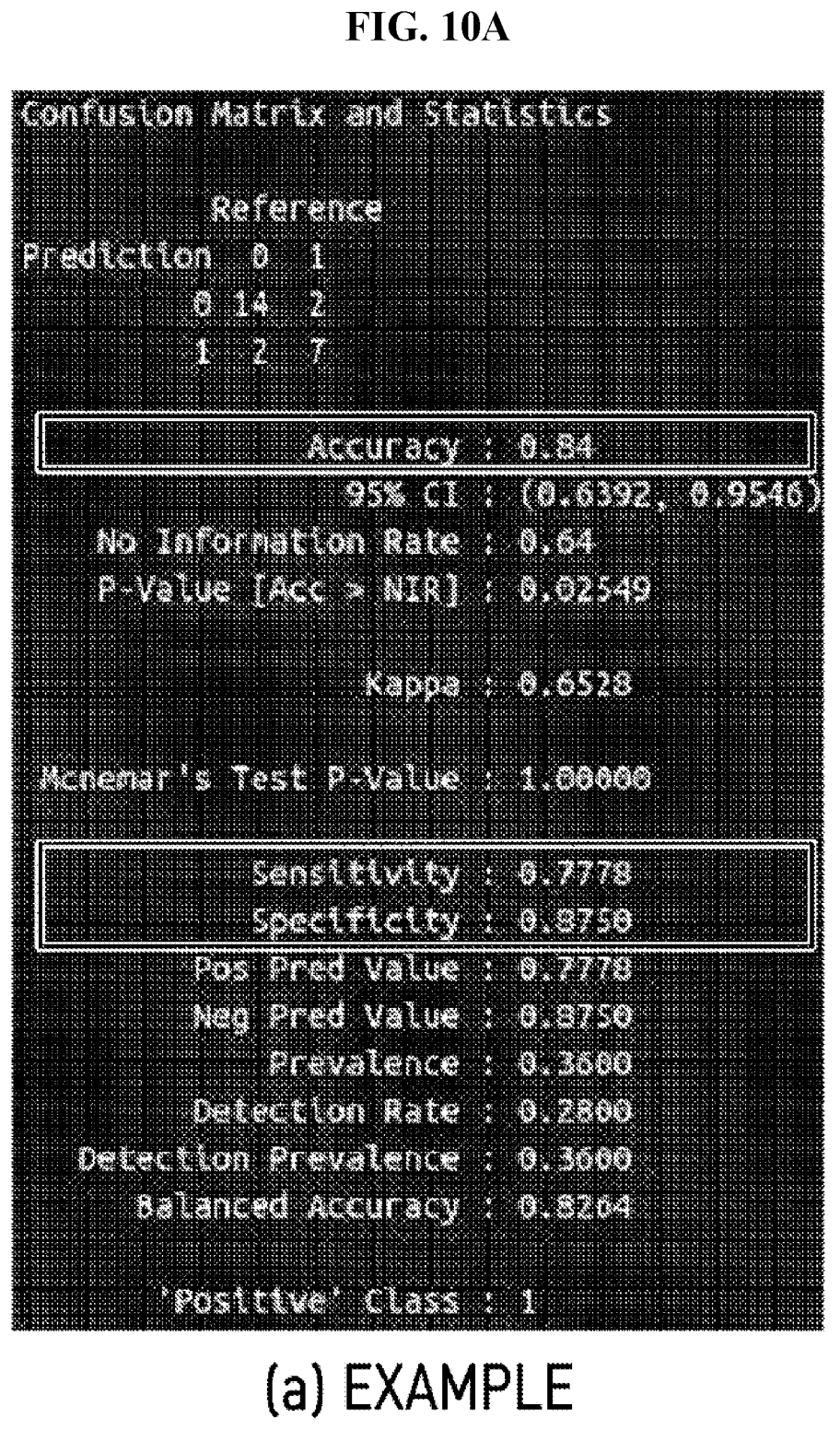

```
Confusion Matrix and Statistics

          Reference
Prediction  0  1
         0 14  2
         1  2  7

               Accuracy : 0.84
                 95% CI : (0.6392, 0.9546)
    No Information Rate : 0.64
    P-Value [Acc > NIR] : 0.02549

                  Kappa : 0.6528

 Mcnemar's Test P-Value : 1.00000

            Sensitivity : 0.7778
            Specificity : 0.8750
         Pos Pred Value : 0.7778
         Neg Pred Value : 0.8750
             Prevalence : 0.3600
         Detection Rate : 0.2800
   Detection Prevalence : 0.3600
      Balanced Accuracy : 0.8264

       'Positive' Class : 1
```

(a) EXAMPLE

FIG. 10B

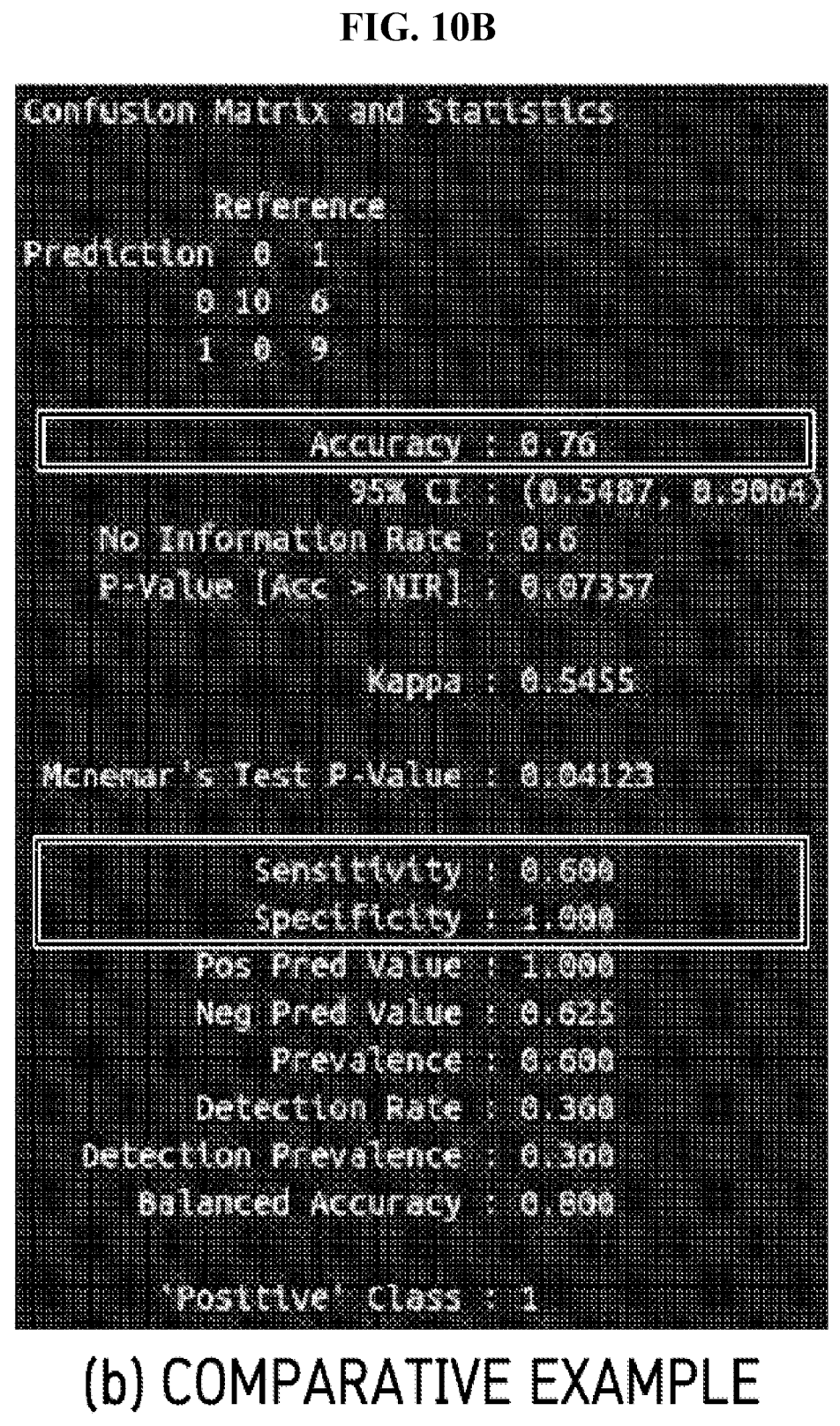

```
Confusion Matrix and Statistics

          Reference
Prediction  0  1
         0 10  6
         1  0  9

               Accuracy : 0.76
                 95% CI : (0.5487, 0.9064)
    No Information Rate : 0.6
    P-Value [Acc > NIR] : 0.07357

                  Kappa : 0.5455

 Mcnemar's Test P-Value : 0.04123

            Sensitivity : 0.600
            Specificity : 1.000
         Pos Pred Value : 1.000
         Neg Pred Value : 0.625
             Prevalence : 0.600
         Detection Rate : 0.360
   Detection Prevalence : 0.360
      Balanced Accuracy : 0.800

       'Positive' Class : 1
```

(b) COMPARATIVE EXAMPLE (a) EXAMPLE (b) COMPARATIVE EXAMPLE (a) EXAMPLE (b) COMPARATIVE EXAMPLE (b) COMPARATIVE EXAMPLE (a) EXAMPLE (b) COMPARATIVE EXAMPLE

METHOD AND DIAGNOSTIC APPARATUS FOR DETERMINING ENTERIC DISORDER USING MACHINE LEARNING MODEL

TECHNICAL FIELD

The present disclosure relates to a method and diagnostic apparatus for determining an enteric disorder using a machine learning model.

BACKGROUND

Enteric disorders are diseases that result in chronic inflammation of unknown causes in the intestinal tract and shows a chronic progress through repetition of worsening and remission. Typical examples thereof include inflammatory bowel diseases, particularly, ulcerative colitis and Crohn's disease.

Until the mid-1980s, inflammatory bowel diseases were difficult to detect in Korea. However, according to the statistics of the National Health Insurance Review and Assessment Service, at the end of 2011, the number of patients with Crohn's disease in Korea was 23,000 and the number of patients with ulcerative colitis was 29,000. In the modern age, the number of patients with enteric disorders has been rapidly increased.

Inflammatory bowel diseases require a considerable amount of time from the onset of symptoms to diagnosis. Crohn's disease usually takes more than a year, and ulcerative colitis usually takes 3 to 6 months. If an enteric disorder is left untreated, digestion or nutrient absorption may not be smooth, which may lead to nutritional deficiencies or nutritional disorders, and further lead to serious complications such as intestinal obstruction/stenosis/perforation. It is even known that patients with inflammatory bowel diseases are twice as likely to develop bowel cancer than normal persons.

As described above, enteric disorders require quick and accurate diagnosis because negative impacts on the human body increase if diagnosis is delayed.

Meanwhile, the term "genome" refers to genes contained in chromosomes, the term "microbiota" refers to a collection of microbes found in a specific environment, and the "microbiome" refers to genes in all the collections of microbes in the environment. Herein, the term "microbiome" may refer to a combination of genome and microbiota.

Recently, there has been an attempt to diagnose an enteric disorder by identifying microbes that can act as causative factors of an enteric disorder through metagenome analysis of microbiota.

In this regard, Korean Patent No. 10-2057047, which is the prior art, relates to a disease prediction apparatus and a disease prediction method using the same, and discloses a disease prediction method for predicting a disease of a predetermined person by comparing a learning vector with a predetermined person vector extracted from a biosignal of the predetermined person.

However, according to the prior art, bacterial metagenome analysis is performed without a special process such as culturing of samples, and, thus, it is difficult to accurately find the causative factor of an enteric disorder due to a large bias between samples of respective subjects.

Also, when a machine learning model is trained using unprocessed samples of respective subjects as training data, the training data may have a lot of noise, and, thus, the performance of the machine learning model may be significantly degraded.

SUMMARY

The present disclosure is to solve the above problems, and is to improve the performance of a machine learning model for diagnosing the presence or absence of an enteric disorder by selecting microbe-related features from multiple microbial data based on an analysis result of a mixture of a sample and a gut environment-like composition.

However, the problems to be solved by this disclosure are not limited to those mentioned above, and other problems not mentioned will be clearly understood by a person with ordinary skill in the art from the following description.

Means for Solving the Problems

To solve the problems, an example of the present disclosure provides a method for determining an enteric disorder by using a machine learning model, including: analyzing a mixture of a gut-derived substance collected from a subject and a gut environment-like composition; extracting multiple microbial data based on an analysis result of the mixture; selecting a microbe-related feature to be used for the machine learning model from the multiple microbial data based on a predetermined feature selection algorithm; training the machine learning model by using the microbe-related feature; and determining an enteric disorder by inputting, into the trained machine learning model, the microbial data collected from a subject to be tested. The microbe-related feature includes the content of at least one kind of microbes selected from genera belonging to the family Tannerellaceae, the family Bifidobacteriaceae, the family Ruminococcaceae, the family Clostridaceae, the family Lachnospiraceae, the family Bacteroidaceae, the family Erysipelatoclostridiaceae, the family Veilonellaceae, the family Bacteroidaceae, the family Ruminococcaceae, the family Lachnospiraceae, and the family Anaerovoracaceae.

Also, another example of the present disclosure provides an apparatus for diagnosing an enteric disorder by using a machine learning model, including: a microbial data extraction unit that extracts multiple microbial data based on an analysis result of a mixture of a gut-derived substance collected from a subject and a gut environment-like composition; a feature selection unit that selects a microbe-related feature to be used for the machine learning model from the multiple microbial data based on a predetermined feature selection algorithm; a training unit that trains the machine learning model by using the microbe-related feature; and a diagnostic unit that diagnoses an enteric disorder by inputting, into the trained machine learning model, the microbial data collected from a subject to be tested. The microbe-related feature includes the content of at least one kind of microbes selected from genera belonging to the family Tannerellaceae, the family Bifidobacteriaceae, the family Ruminococcaceae, the family Clostridaceae, the family Lachnospiraceae, the family Bacteroidaceae, the family Erysipelatoclostridiaceae, the family Veilonellaceae, the family Bacteroidaceae, the family Ruminococcaceae, the family Lachnospiraceae, and the family Anaerovoracaceae.

The above-described problem solving means are merely illustrative and should not be construed as intended to limit the present disclosure. In addition to the above-described exemplary embodiments, there may be additional embodiments described in the drawings and detailed descriptions of the invention.

Effects of the Invention

According to any one of the above-described means for solving the problems of the present disclosure, it is possible to improve the performance of a machine learning model for diagnosing the presence or absence of an enteric disorder by selecting microbe-related features from multiple microbial data based on an analysis result of a mixture of a sample and a gut environment-like composition.

BRIEF DESCRIPTION OF THE DRAWINGS

FIGS. 6C-6D are diagrams for explaining the importance of selected microbe-related features.

FIGS. 8A and 8B are a diagram comparing analysis results of respective samples according to an enteric disorder determination method of an example of the present disclosure and a method of a comparative example.

FIGS. 10A-10B are diagrams comparing XGB models in terms of performance according to an enteric disorder determination method of an example of the present disclosure and a method of a comparative example.

DETAILED DESCRIPTIONS OF EXEMPLARY EMBODIMENTS

Figure 1:
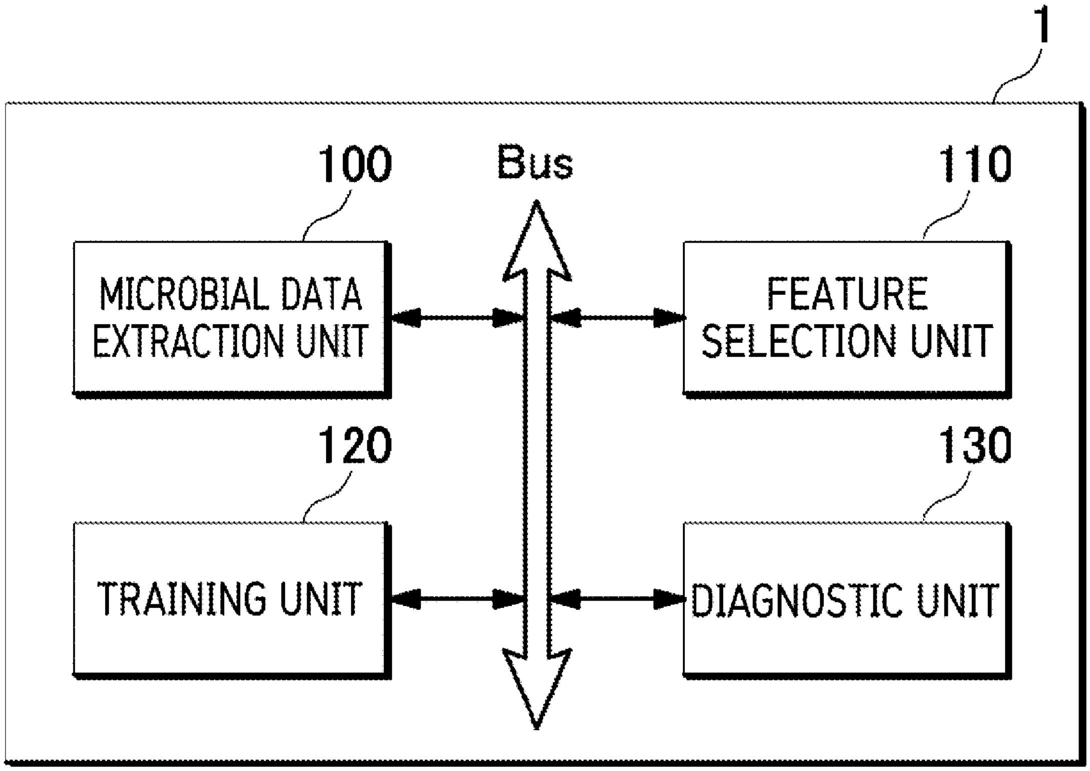
FIG. 1 is a block diagram illustrating a diagnostic apparatus according to an example of the present disclosure.
Figure 2:
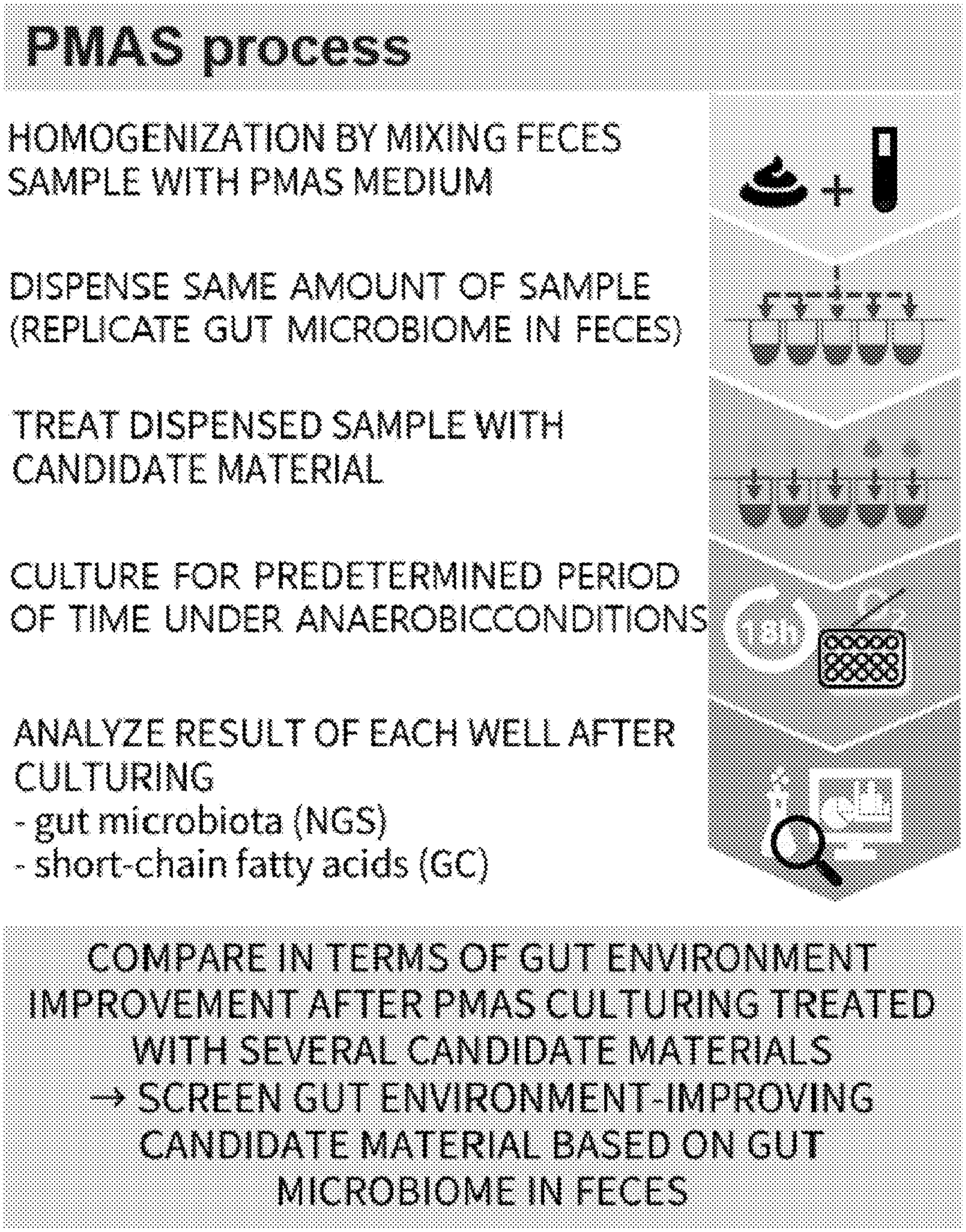
FIG. 2 is a diagram illustrating an MCMOD technique according to an example of the present disclosure.
Figure 3:
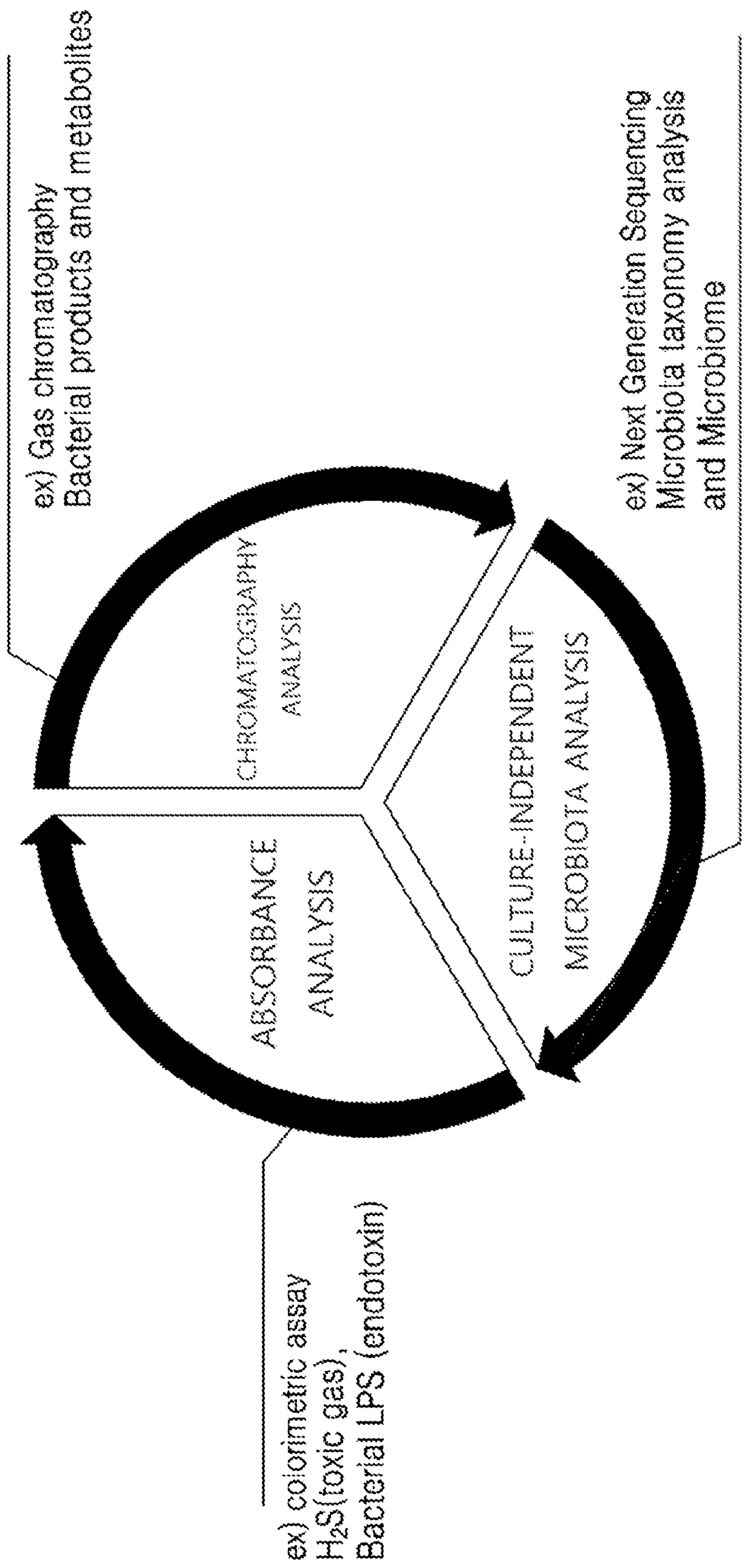
FIG. 3 is a diagram for explaining a sample analysis through the MCMOD technique according to an example of the present disclosure.
Figure 4:
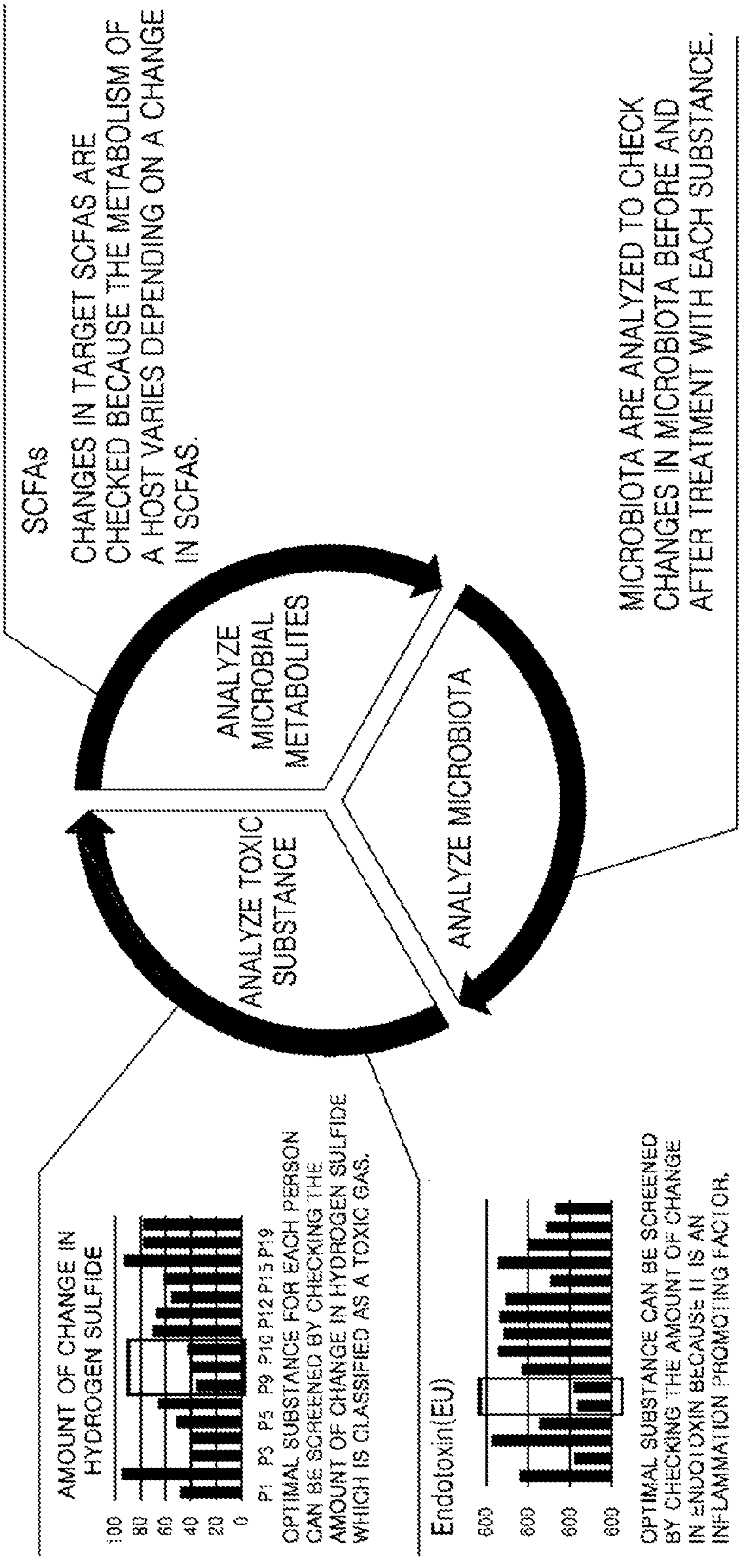
FIG. 4 is a diagram for explaining an interpretation of a sample analysis result through the MCMOD technique according to an example of the present disclosure.

Hereafter, examples of the present disclosure will be described in detail with reference to the accompanying drawings so that the present disclosure may be readily implemented by a person with ordinary skill in the art. However, it is to be noted that the present disclosure is not limited to the examples but may be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element. Further, it is to be understood that the term "comprises or includes" and/or "comprising or including" used in the document means that one or more other components, steps, operation and/or existence or addition of elements are not excluded in addition to the described components, steps, operation and/or elements unless context dictates otherwise and is not intended to preclude the possibility that one or more other features, numbers, steps, operations, components, parts, or combinations thereof may exist or may be added.

Throughout the whole document, the term "unit" includes a unit implemented by hardware or software and a unit implemented by both of them. One unit may be implemented by two or more pieces of hardware, and two or more units may be implemented by one piece of hardware.

In the present specification, some of operations or functions described as being performed by a device may be performed by a server connected to the device. Likewise, some of operations or functions described as being performed by a server may be performed by a device connected to the server.

Hereinafter, examples of the present disclosure will be described in detail with reference to the accompanying drawings.

FIG. 1 is a block diagram illustrating a diagnostic apparatus according to an example of the present disclosure. Referring to FIG. 1, a diagnostic apparatus 1 may include a microbial data extraction unit 100, a feature selection unit 110, a training unit 120, and a diagnostic unit 130. The diagnostic apparatus 1 of the present disclosure may be an apparatus configured to determine the presence or absence of an enteric disorder.

Examples of the diagnostic apparatus 1 may include a personal computer such as a desktop computer or a laptop computer, as well as a mobile device capable of wired/wireless communication. The mobile device is a wireless communication device that ensures portability and mobility and may include a smartphone, a tablet PC, a wearable device and various kinds of devices equipped with a communication module such as Bluetooth (BLE, Bluetooth Low Energy), NFC, RFID, ultrasonic waves, infrared rays, WiFi, LiFi, and the like. However, the diagnostic apparatus 1 is not limited to the embodiment illustrated in FIG. 1 or the above examples.

The diagnostic apparatus 1 may detect a biomarker for diagnosing the presence or absence of an enteric disorder caused by abnormalities in the gut environment in a sample collected from a subject.

For example, the diagnostic apparatus 1 may diagnose the presence or absence of an enteric disorder based on a sample preparation process, a sample pretreatment process, a sample analysis process, a data analysis process, and derived data. In the present disclosure, the term "diagnosis" may refer to determining or predicting the presence or absence of an enteric disorder based on the output value of a machine learning model.

In an embodiment, the biomarker may be a substance detected in the gut, and specifically, it may include microbiota, endotoxins, hydrogen sulfide, gut microbial metabolites, short-chain fatty acids and the like, but is not limited thereto.

The microbial data extraction unit 100 may extract multiple microbial data based on an analysis result of a mixture of a sample collected from a subject and a gut environment-like composition. Herein, the multiple microbial data may be classified into a training set to be used for training and a test set, and a classification ratio may vary, such as 9:1, 7:3, 5:5 and the like, and may be preferably 7:3.

According to the present disclosure, pretreatment for analyzing a mixture of a sample and a gut environment-like composition is performed. In the present disclosure, the pretreatment may be referred to as MCMOD (Meta-culture Multi-Omics Diagnose).

For example, an in-vitro analysis of fecal microbiome and metabolites is performed to feces samples obtained from humans and various animals that can most easily represent the gut microbial environment in vivo.

Herein, the term "subject" refers to any living organism which may have a gut disorder, may have a disease caused by a gut disorder or develop it or may be in need of an improvement of gut environment. Specific examples thereof may include, but not limited to, mammals such as mice, monkeys, cattle, pigs, minipigs, domestic animals and humans, birds, cultured fish, and the like.

The term "sample" refers to a material derived from the subject, and may be, for example, a material derived from the intestine.

Specifically, the "sample" may be cells, urine, feces, or the like, but is not limited thereto as long as a material, such as microbiota, gut microbial metabolites, endotoxins and short-chain fatty acids, present in the gut can be detected therefrom.

The term "gut environment-like composition" may refer to a composition prepared for identically or similarly mimicking the gut environment of the subject in vitro. For example, the gut environment-like composition may be a culture medium composition, but is not limited thereto.

The gut environment-like composition may include L-cysteine hydrochloride and mucin.

Herein, the term "L-cysteine hydrochloride" is one of amino acid supplements and plays an important role in metabolism as a component of glutathione in vivo and is also used to inhibit browning of fruit juices and oxidation of vitamin C.

L-cysteine hydrochloride may be contained at a concentration of, for example, from 0.001% (w/v) to 5% (w/v), specifically from 0.01% (w/v) to 0.1% (w/v).

L-cysteine hydrochloride is one of various formulations or forms of L-cysteine, and the composition may include L-cysteine including other types of salts as well as L-cysteine.

The term "mucin" is a mucosubstance secreted by the mucous membrane and includes submandibular gland mucin and others such as gastric mucosal mucin and small intestine mucin. Mucin is one of glycoproteins and known as one of energy sources such as carbon sources and nitrogen sources that gut microbiota can actually use.

Mucin may be contained at a concentration of, for example, 0.01% (w/v) to 5% (w/v), specifically, from 0.1% (w/v) to 1% (w/v), but is not limited thereto.

In an embodiment, the gut environment-like composition may not include any nutrient other than mucin, and specifically may not include a nitrogen source and/or carbon source such as protein and carbohydrate.

The protein that serves as a carbon source and nitrogen source may include one or more of tryptone, peptone and yeast extract, but is not limited thereto. Specifically, the protein may be tryptone.

The carbohydrate that serves as a carbon source may include one or more of monosaccharides such as glucose, fructose and galactose and disaccharides such as maltose and lactose, but is not limited thereto. Specifically, the carbohydrate may be glucose.

In an embodiment, the gut environment-like composition may not include glucose and tryptone, but is not limited thereto.

The gut environment-like composition may further include one or more selected from the group consisting of sodium chloride (NaCl), sodium carbonate ($NaHCO_3$), potassium chloride (KCl) and hemin. Specifically, sodium chloride may be contained at a concentration of, for example, from 10 mM to 100 mM, sodium carbonate may be contained at a concentration of, for example, from 10 mM to 100 mM, potassium chloride may be contained at a concentration of, for example, from 1 mM to 30 mM, and hemin may be contained at a concentration of, for example, from $1\times10^{-6}$ g/L to $1\times10^{-4}$ g/L, but the present disclosure is not limited thereto.

In the pretreatment, the mixture may be cultured for 18 to 24 hours under anaerobic conditions.

For example, in an anaerobic chamber, the same amount of a homogenized feces-medium mixture is dispensed to each of culture plates such as 96-well plates. Herein, the culture may be performed for 12 hours to 48 hours, specifically, for 18 hours to 24 hours, but is not limited thereto.

Then, the plates are cultured under anaerobic conditions with temperature, humidity and motion similar to those of the gut environment to ferment and culture the respective test groups.

After the culturing of the mixture, a culture in which the mixture has been cultured is analyzed. The analysis of the culture may be to extract microbial data including at least one of the content, concentration and kind of one or more of endotoxins, hydrogen sulfides, short-chain fatty acids (SCFAs) and microbiota-derived metabolites contained in the culture, and a change in kind, concentration, content or diversity of bacteria included in the microbiota, but is not limited thereto.

Herein, the term "endotoxin" is a toxic substance that can be found inside a bacterial cell and acts as an antigen composed of a complex of proteins, polysaccharides, and lipids. In an embodiment, the endotoxin may include lipopolysaccharides (LPS), but is not limited thereto, and the LPS may be specifically gram negative and pro-inflammatory.

The term "short-chain fatty acid (SCFA)" refers to a short-length fatty acid with six or fewer carbon atoms and is a representative metabolite produced from gut microbes. The SCFA has useful functions in the body, such as an increase in immunity, stabilization of gut lymphocytes, a decrease in insulin signaling, and stimulation of sympathetic nerves.

In an embodiment, the short-chain fatty acids may include one or more selected from the group consisting of formate, acetate, propionate, butyrate, isobutyrate, valerate and isovalerate, but are not limited thereto.

The culture may be analyzed by various analysis methods, such as genetic analysis methods including absorbance analysis, chromatography analysis and next generation sequencing, and metagenomic analysis methods, that can be used by a person with ordinary skill in the art.

When the culture is analyzed, the culture may be centrifuged to separate a supernatant and a precipitate and then, the supernatant and the precipitate (pallet) may be analyzed. For example, metabolites, short-chain fatty acids, toxic substances, etc. from the supernatant and microbiota from the pallet may be analyzed.

For example, after the culturing is completed, toxic substances, such as hydrogen sulfide and bacterial LPS (endotoxin), microbial metabolites, such as short-chain fatty acids, from the supernatant obtained by centrifugation of the cultured test groups are analyzed through absorbance analysis and chromatography analysis, and a culture-independent analysis method is performed to the microbiota from the centrifuged pellet. For example, the amount of change in hydrogen sulfide produced by the culturing may be measured through a methylene blue method using N,N-dimethyl-p-phenylene-diamine and iron chloride (FeCl3) and the level of endotoxins that is one of inflammation promoting factors may be measured using an endotoxin assay kit. Also, microbial metabolites such as short-chain fatty acids including acetate, propionate and butyrate can be analyzed through gas chromatography.

Microbiota can be analyzed by genome-based analysis through metagenomic analysis such as real-time PCR in which all genomes are extracted from a sample and a bacteria-specific primer suggested in the GULDA method, or next generation sequencing.

According to the present disclosure, the culture is analyzed in a state where the gut environment is implemented in vitro by using the gut environment-like composition, and, thus, it is possible to reduce a bias between training data by optimizing the training data before machine learning.

Accordingly, it is possible to facilitate selection of microbe-related features to be described later and also improve the performance of a machine learning model by training the machine learning model based on the microbe-related features. Therefore, it is possible to increase the accuracy in diagnosing the presence or absence of an enteric disorder through the trained machine learning model.

The feature selection unit 110 may perform selection (i.e., feature selection) of microbe-related features from multiple microbial data as features to be used for the machine learning model based on a predetermined feature selection algorithm. The number of the microbe-related features may be 1 to 23. For example, the optimal number of the microbe-related features may be 14.

Features (variables or attributes) are used in creating a machine learning model. If a large number of features or inappropriate features are used, the machine learning model may overfit data or the prediction accuracy may decrease.

Accordingly, in order for the machine learning model to have a high prediction accuracy, it is necessary to use an appropriate combination of features. That is, it is possible to reduce the complexity of the machine learning model while using as few features as possible by selecting features most closely related to a response feature to be predicted.

The feature selection algorithm may include at least one of, for example, a Boruta algorithm and a recursive feature elimination (RFE) algorithm.

The microbe-related features selected from a predetermined feature selection algorithm may include the content of at least one kind of microbes selected from genera belonging to the family Tannerellaceae, the family Bifidobacteriaceae, the family Ruminococcaceae, the family Clostridaceae, the family Lachnospiraceae, the family Bacteroidaceae, the family Erysipelatoclostridiaceae, the family Veilonellaceae, the family Bacteroidaceae, the family Ruminococcaceae, the family Lachnospiraceae, and the family Anaerovoraceae.

In an embodiment, the microbe-related features selected from a predetermined feature selection algorithm may include the content of at least one kind of microbes selected from species belonging to, for example, the genus Parabacteroides, the genus *Bifidobacterium*, the genus Subdoligranulum, the genus *Clostridium*, the genus Ruminococcus, the genus *Bacteroides*, the genus Erysipelatoclostridium, the genus RF39, the genus *Veillonella*, the genus *Bacteroides*, the genus *Eubacterium*, the genus GCA.900066575, and the genus UCG.010.

The training unit 120 may train the machine learning model with the microbe-related features.

For example, the training unit 120 may train machine learning model to predict whether an enteric disorder is present for each of microbial data by performing supervised learning based on labeling of whether an enteric disorder is present for each of the microbial data (training data) and the content of microbes related to the selected feature.

The machine learning model may include at least one of, for example, a linear regress analysis (LRA) model, a random forest model, a generalized linear (GLM) model, a gradient boosting model, and an extreme gradient boosting (XGB) model.

The diagnostic unit 130 may diagnose an enteric disorder by inputting, into the trained machine learning model, the microbial data collected from a subject to be tested.

For example, the diagnostic unit 130 may diagnose an enteric disorder based on whether an enteric disorder is present, which is an output value of the machine learning model. That is, the diagnostic unit 130 may determine whether the subject has an enteric disorder or predict the incidence of an enteric disorder of the subject based on the output value of the machine learning model.

Hereinafter, Examples of the present disclosure will be described in detail. However, the present disclosure is not limited thereto.

EXAMPLES

Example 1. Microbe-Related Feature Selected Based on Recursive Feature Elimination Algorithm after or without MCMOD Treatment In order to check microbe-related features selected based on a recursive feature elimination algorithm after or without MCMOD treatment of Example 1, a test was performed as follows.

According to the present disclosure, a pretreatment is performed to analyze a mixture of a sample and a gut environment-like composition. In the present disclosure, the above-described pretreatment may be referred to as MCMOD. Meanwhile, in the present disclosure, Comparative Example relates to a method for determining an enteric disorder based on microbial data extracted by performing only a conventional pretreatment without performing the above-described pretreatment on a sample. In this regard, the conventional pretreatment for Comparative Example is referred to as SMOD.

As shown in Table 1 below, samples were microbial data from MCMOD and SMOD of a simple clinical data set (feces) based on questionnaire results received from 62 enteric disorder patients (disease group) and 136 normal people (normal group). In particular, oversampling and undersampling were performed on the data set to reduce class imbalance, and the data set was transformed into a total of 200 data sets including 104 normal data and 96 enteric disorder data.

TABLE 1

| Disease and Examination Item | Classification | Data Source (Collection Route) | Criteria for Disease | MOD | Number of Samples from Original Data: Disease Group | Normal Group | Total | Oversampled data: Train Set: Disease Group | Normal Group | Total | Test Set: Disease Group | Normal Group | Total |
|---|---|---|---|---|---|---|---|---|---|---|---|---|---|
| Presence or Absence of Enteric Disorder | Medical Questionnaire | HEM Service Experience Group | Self-report | MCMOD | 31 | 68 | 99 | 39 | 36 | 75 | 9 | 16 | 25 |
| | | | | SMOD | 31 | 68 | 99 | 33 | 42 | 75 | 15 | 10 | 25 |

Microbial data were classified into training data (Train set) to be used for learning and test data (Test set) at a ratio of 7:3.

Then, feature selection was performed on the training data through the Boruta algorithm, a binomial deviance plot, and the XGB model to select microbe-related features to be used in the machine learning model. Meanwhile, as will be described below, the test data were used to assess the performance of the machine learning model.

Table 2 shows a result of primary selection of features through the Boruta algorithm according to an enteric disorder determination method of Example of the present disclosure and Table 3 shows a result of primary selection of features through the Boruta algorithm according to a method of Comparative Example. As a result of primary selection of features from among a total of 978 features, 59 features for the MCMOD and 63 features for the SMOD were selected.

TABLE 2

| | Final Decision |
|---|---|
| Tannerellaceae_*Parabacteroides*_*Parabacteroides*_sp. | Confirmed |
| Lachnospiraceae_Lachnoclostridium_NA | Confirmed |
| Bacteroidaceae_*Bacteroides*_NA | Confirmed |
| Ruminococcaceae_*Faecalibacterium*_NA | Confirmed |
| Lachnospiraceae_Anaerostipes_NA | Confirmed |
| Clostridiaceae_*Clostridium*_sensu_stricto_1_uncultured_bacterium | Confirmed |
| *Clostridia_vadin*BB60_group_*Clostridia_vadin*BB60_group_uncultured_prokaryote | Confirmed |
| Lachnospiraceae_.*Ruminococcus.*_*gauvreauii*_group_NA | Confirmed |
| Bacteroidaceae_*Bacteroides*_Bacteroidaceae_bacterium | Confirmed |
| Ruminococcaceae_Subdoligranulum_NA | Confirmed |
| Lachnospiraceae_.*Ruminococcus.*_*torques*_group_NA | Confirmed |
| Christensenellaceae_Christensenellaceae_R.7_group_human_gut | Confirmed |
| Coriobacteriales_Incertae_Sedis_Raoultibacter_Raoultibacter_timonensis | Confirmed |
| Bifidobacteriaceae_*Bifidobacterium*_NA | Confirmed |
| Lachnospiraceae_Fusicatenibacter_NA | Confirmed |
| Erysipelotrichaceae_Holdemanella_uncultured_bacterium | Confirmed |

TABLE 2-continued

| | Final Decision |
|---|---|
| Veillonellaceae_*Dialister*_NA | Confirmed |
| Erysipelatoclostridiaceae_*Erysipelatoclostridium_Erysipelatoclostridium_ramosum* | Confirmed |
| Clostridiaceae_*Clostridium_sensu_stricto*_1_NA | Confirmed |
| Rikenellaceae_*Alistipes_Alistipes_putredinis* | Confirmed |
| UCG.010_UCG.010_NA | Confirmed |
| Clostridia_UCG.014_*Clostridia*_UCG.014_uncultured_bacterium | Confirmed |
| Rikenellaceae_*Alistipes_Alistipes_shahii* | Confirmed |
| Peptostreptococcaceae_NA_NA | Confirmed |
| RF39_RF39_gut_metagenome | Confirmed |
| Lachnospiraceae_GCA.900066575_uncultured_bacterium | Confirmed |
| Prevotellaceae_*Prevotella_Prevotella_stercorea* | Confirmed |
| Oscillospiraceae_UCG.005_NA | Confirmed |
| *Lactobacillus_Lactobacillus_Lactobacillus_sakei* | Confirmed |
| Ruminococcaceae_.*Eubacterium.*_*siraeum*_group_.*Eubacterium.*_*siraeum* | Confirmed |
| UCG.010_UCG.010_uncultured_bacterium | Confirmed |
| Anaerovoracaceae_Family_XIII_AD3011_group_NA | Confirmed |
| Erysipelotrichaceae_*Holdemania_Holdemania_filiformis* | Confirmed |
| Streptococcaceae_*Streptococcus_Streptococcus_vestibularis* | Confirmed |
| Marinifilaceae_Butyricimonas_uncultured_bacterium | Confirmed |
| Veillonellaceae_*Dialister*_uncultured_bacterium | Confirmed |
| Veillonellaceae_*Veillonella*_NA | Confirmed |
| UCG.010_UCG.010_gut_metagenome | Confirmed |
| Barnesiellaceae_Barnesiella_NA | Confirmed |
| Eggerthellaceae_Enterorhabdus_uncultured_bacterium | Confirmed |
| Oscillospiraceae_uncultured_uncultured_bacterium | Confirmed |
| Lachnospiraceae_.*Ruminococcus.*_*torques*_group_*Ruminococcus*_sp. | Confirmed |
| Desulfovibrionaceae_*Bilophila*_uncultured_bacterium | Confirmed |
| Enterobacteriaceae_*Escherichia.Shigella_Streptomyces*_sp. | Confirmed |
| Akkermansiaceae_*Akkermansia*_uncultured_*Akkermansia* | Confirmed |
| Ruminococcaceae_Negativibacillus_uncultured_bacterium | Confirmed |
| Erysipelatoclostridiaceae_*Coprobacillus*_uncultured_bacterium | Confirmed |
| RF39_RF39_human_gut | Confirmed |
| Erysipelotrichaceae_*Turicibacter*_uncultured_bacterium | Confirmed |
| UCG.010_UCG.010_metagenome | Confirmed |
| Enterobacteriaceae_Kosakonia_NA | Confirmed |
| Staphylococcaceae_*Staphylococcus*_NA | Confirmed |
| Ruminococcaceae_Angelakisella_*Ruminococcus*_sp. | Confirmed |
| Lactobacillaceae_*Lactobacillus_bacterium*_ii1348 | Confirmed |
| Staphylococcaceae_*Staphylococcus_Staphylococcus_sciuri* | Confirmed |
| Lachnospiraceae_*Coprococcus_Coprococcus_comes* | Confirmed |
| Butyricicoccaceae_Butyricicoccus_Agathobaculum_butyriciproducens | Confirmed |
| Campylobacteraceae_*Campylobacter_Campylobacter_hominis* | Confirmed |
| Eggerthellaceae_Enterorhabdus_mouse_gut | Confirmed |

TABLE 3

| | Final Decision |
|---|---|
| Ruminococcaceae_CAG.352_uncultured_bacterium | Confirmed |
| Tannerellaceae_*Parabacteroides_Parabacteroides*_sp. | Confirmed |
| Bacteroidaceae_*Bacteroides*_NA | Confirmed |
| Ruminococcaceae_*Faecalibacterium*_NA | Confirmed |
| Lachnospiraceae_Lachnoclostridium_NA | Confirmed |
| Monoglobaceae_Monoglobus_NA | Confirmed |
| Ruminococcaceae_*Ruminococcus*_metagenome | Confirmed |
| Lachnospiraceae_.*Ruminococcus.*_*gauvreauii*_group_NA | Confirmed |
| *Clostridia_vadin*BB60_group_*Clostridia_vadin*BB60_group_uncultured_prokaryote | Confirmed |
| Enterococcaceae_*Enterococcus*_NA | Confirmed |
| Actinomycetaceae_*Actinomyces*_NA | Confirmed |
| Saccharimonadaceae_NA_NA | Confirmed |
| Lachnospiraceae_*Roseburia*_NA | Confirmed |
| Clostridiaceae_*Clostridium_sensu_stricto*_1_uncultured_bacterium | Confirmed |
| Clostridiaceae_*Clostridium_sensu_stricto*_1_NA | Confirmed |
| *Clostridia*_UCG.014_*Clostridia*_UCG.014_NA | Confirmed |
| Clostridiaceae_*Clostridium_sensu_stricto*_13_*Clostridium*_sp. | Confirmed |
| Bifidobacteriaceae_*Bifidobacterium*_NA | Confirmed |
| Tannerellaceae_*Parabacteroides_Parabacteroides_distasonis* | Confirmed |
| Prevotellaceae_*Prevotella*_uncultured_organism | Confirmed |
| Lachnospiraceae_Blautia_uncultured_bacterium | Confirmed |
| *Lactobacillus_Lactobacillus*_NA | Confirmed |
| Oscillospiraceae_NA_NA | Confirmed |
| Peptostreptococcaceae_Romboutsia_NA | Confirmed |
| Ruminococcaceae_*Faecalibacterium*_uncultured_bacterium | Confirmed |

TABLE 3-continued

| | Final Decision |
|---|---|
| *Lactobacillus_Lactobacillus_Lactobacillus_mucosae* | Confirmed |
| Oscillospiraceae_UCG.002_NA | Confirmed |
| Saccharimonadaceae_TM7a_uncultured_bacterium | Confirmed |
| Pseudomonadaceae_*Pseudomonas*_uncultured_bacterium | Confirmed |
| Rikenellaceae_*Alistipes_Alistipes_shahii* | Confirmed |
| *Lactobacillus_Lactobacillus*_unidentified | Confirmed |
| Lachnospiraceae_.*Ruminococcus._torques*_group_uncultured_bacterium | Confirmed |
| RF39_RF39_uncultured_bacterium | Confirmed |
| Christensenellaceae_Christensenellaceae_R.7_group_NA | Confirmed |
| Peptostreptococcaceae_NA_NA | Confirmed |
| Chloroplast_Chloroplast_NA | Confirmed |
| Streptococcaceae_*Streptococcus_Streptococcus_sanguinis* | Confirmed |
| Methanobacteriaceae_*Methanobrevibacter*_uncultured_rumen | Confirmed |
| Rikenellaceae_*Alistipes*_uncultured_bacterium | Confirmed |
| Lachnospiraceae_.*Eubacterium._eligens*_group_NA | Confirmed |
| Monoglobaceae_Monoglobus_uncultured_organism | Confirmed |
| Actinomycetaceae_*Actinomyces_Actinomyces_pacaensis* | Confirmed |
| UCG.010_UCG.010_NA | Confirmed |
| Ruminococcaceae_*Subdoligranulum*_uncultured_bacterium | Confirmed |
| *Lactobacillus_Lactobacillus_Lactobacillus_fuchuensis* | Confirmed |
| Butyricicoccaceae_UCG.009_uncultured_bacterium | Confirmed |
| Lachnospiraceae_uncultured_bacterium_enrichment | Confirmed |
| Marinifilaceae_Butyricimonas_uncultured_organism | Confirmed |
| Lachnospiraceae_Agathobacter_*Eubacterium*_ramulus | Confirmed |
| Lachnospiraceae_*Coprococcus*_NA | Confirmed |
| Ruminococcaceae_*Candidatus*_Soleaferrea_Ruminococcaceae_bacterium | Confirmed |
| Bacteroidaceae_*Bacteroides*_uncultured_bacterium | Confirmed |
| Lachnospiraceae_Lachnospiraceae_UCG.010_uncultured_bacterium | Confirmed |
| Gemellaceae_*Gemella_Gemella_sanguinis* | Confirmed |
| Tannerellaceae_*Parabacteroides*_uncultured_*Parabacteroides* | Confirmed |
| Ruminococcaceae_Incertae_Sedis_*Clostridium_jeddahense* | Confirmed |
| Peptostreptococcales._Tissierellales_Ezakiella_NA | Confirmed |
| Peptostreptococcaceae_Terrisporobacter_NA | Confirmed |
| Bacteroidaceae_*Bacteroides_Bacteroides*_barnesiae | Confirmed |
| Christensenellaceae_*Christensenella_Christensenella*_sp. | Confirmed |
| Oscillospiraceae_UCG.003_NA | Confirmed |
| Oscillospiraceae_Intestinimonas_uncultured_bacterium | Confirmed |
| Sphingomonadaceae_*Sphingomonas_Sphingomonas_spermidinifaciens* | Confirmed |

Figure 5A:
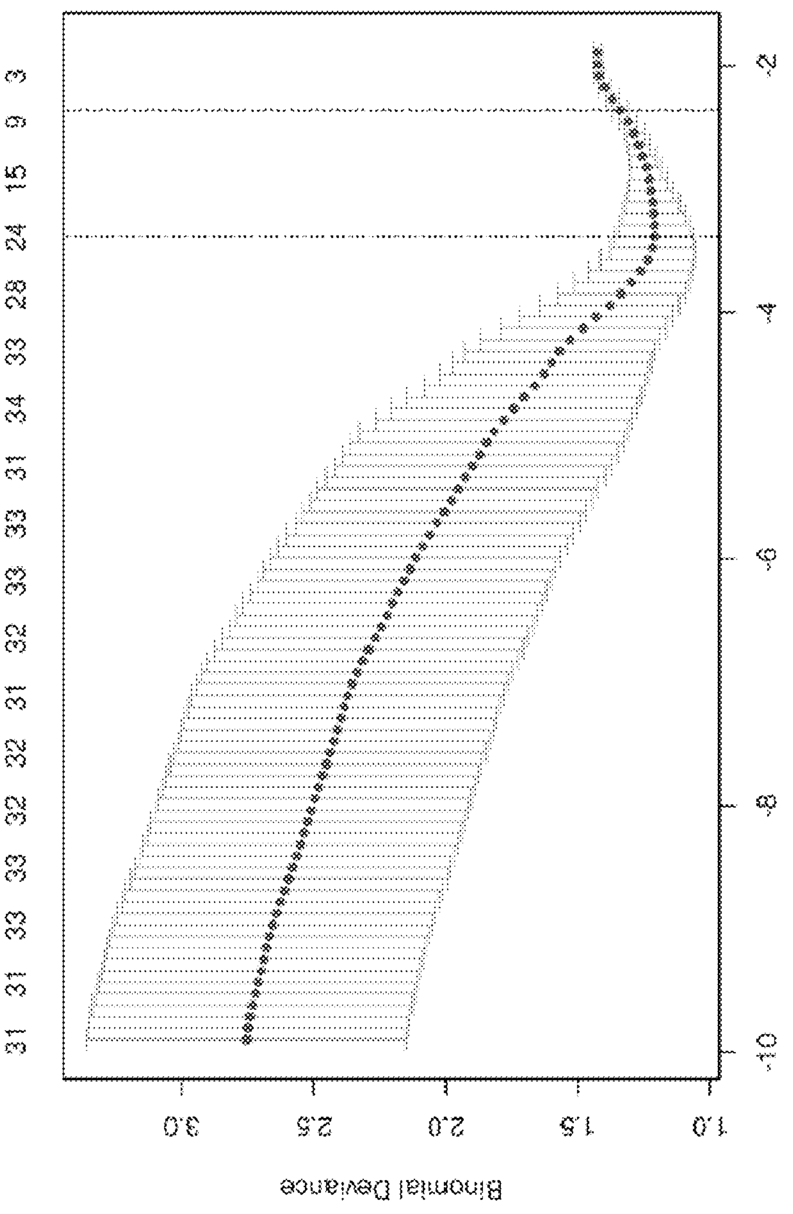
FIGS. 5A-5B are diagrams showing an optimal range of the number of features by checking an error value depending on the number of features through a binomial deviance plot of analysis results according to a method for determining an enteric disorder of an example of the present disclosure and a method of a comparative example.
Figure 5B:
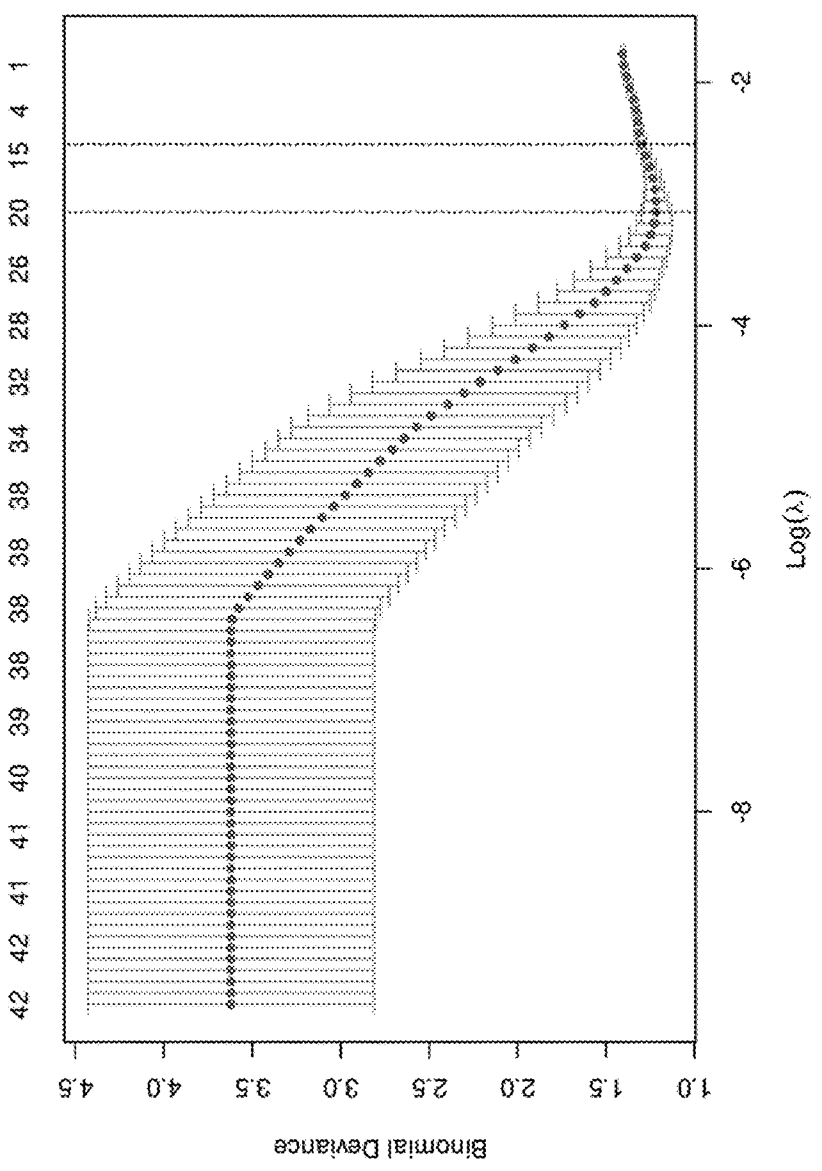
Figure 6A:
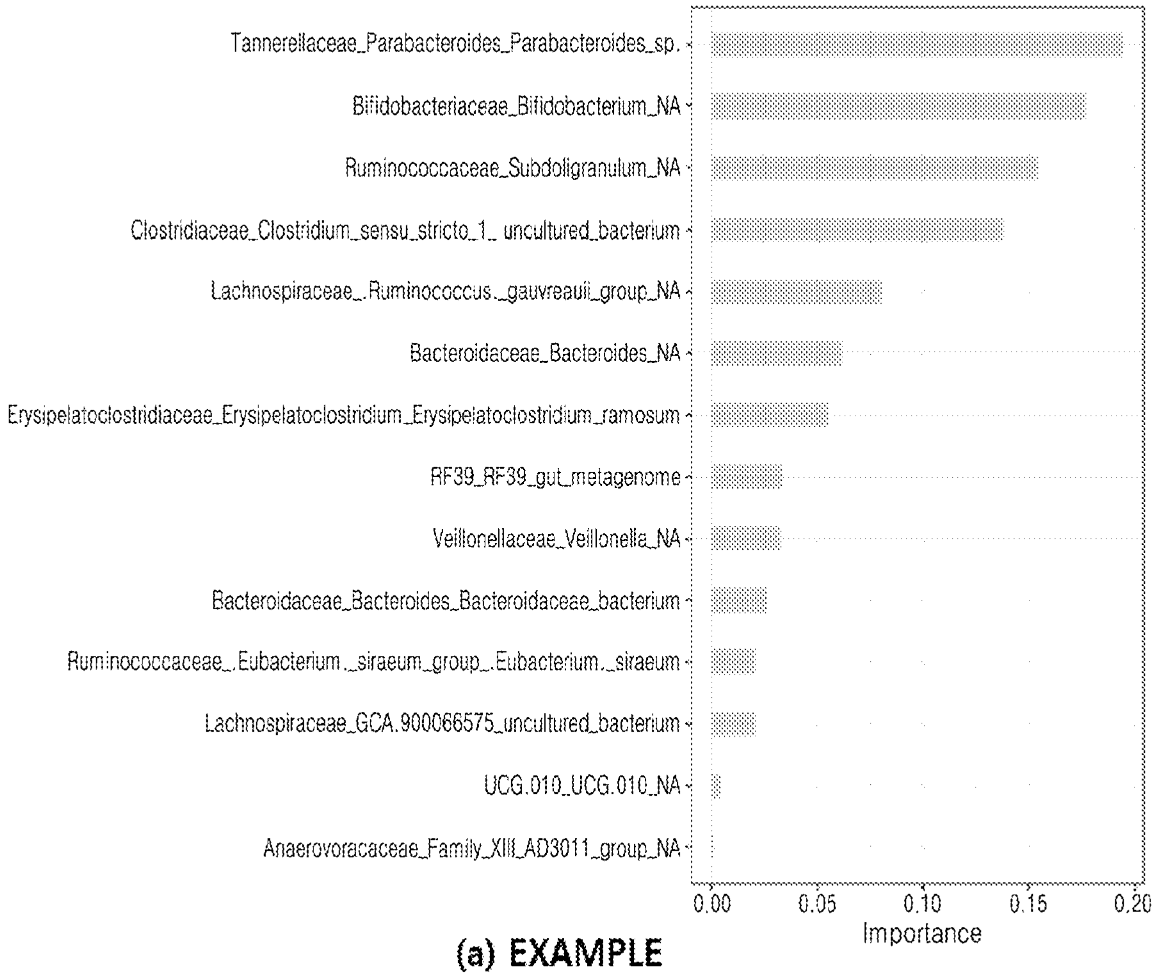
FIGS. 6A-6B are diagrams for explaining the importance of selected microbe-related features.
Figure 6B:
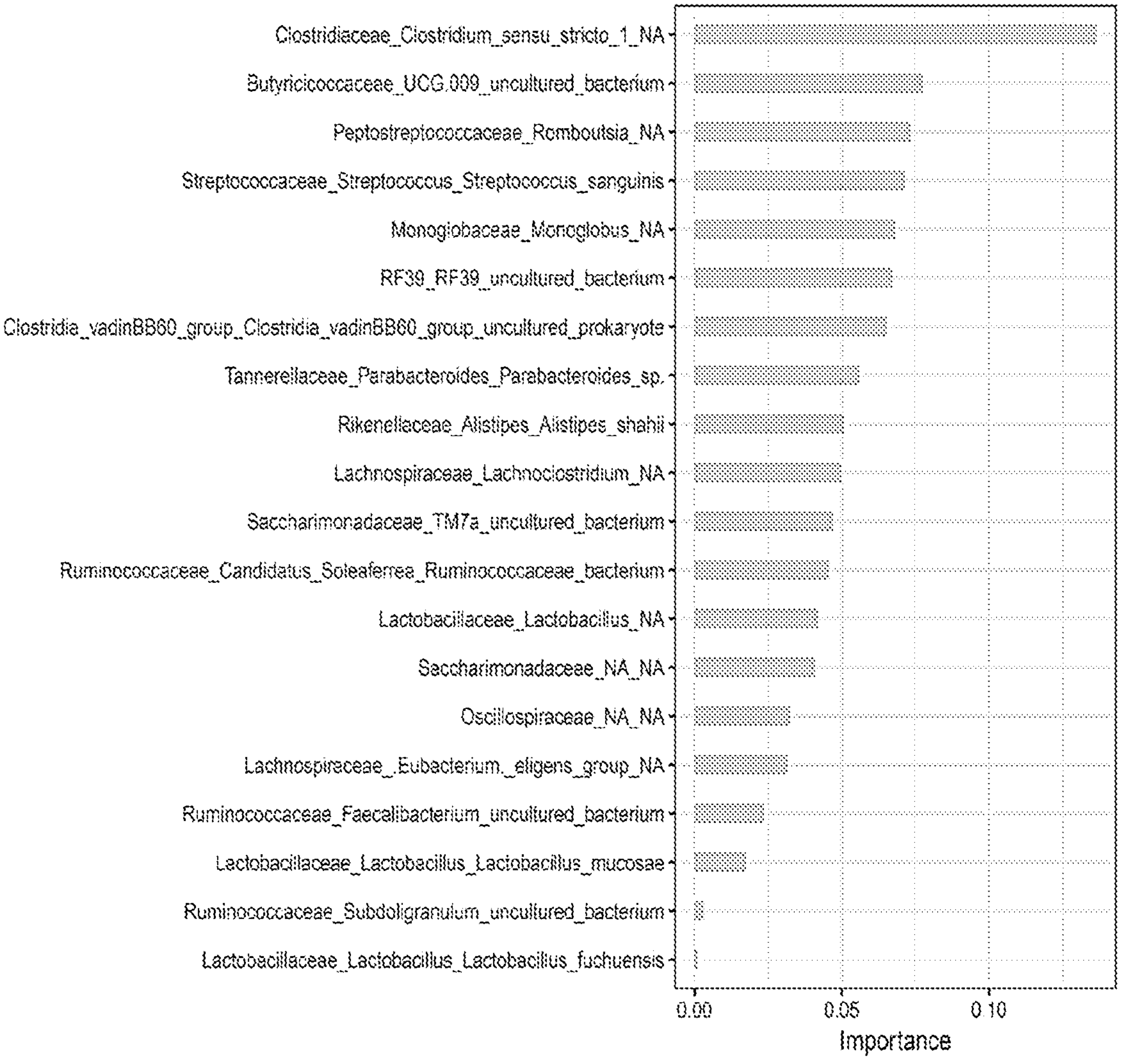

FIGS. 5A-5B are diagrams showing an optimal range of the number of features by checking an error value depending on the number of features through a binomial deviance plot of analysis results according to a method for determining an enteric disorder of Example of the present disclosure and a method of Comparative Example. As a result of checking the number of features suitable for model prediction, the number of features for the MCMOD was 1 to 23 and the number of features for the SMOD was 15 to 20.

FIGS. 6A-6D are diagrams for explaining the importance of selected microbe-related features. Multiple microbe-related features selected through the XGB model may be selected. FIGS. 6A-6D shows 14 microbe-related features with high accuracy for the MCMOD and 20 microbe-related features with high accuracy for the SMOD.

For example, in the MCMOD, a microbe-related feature with high accuracy among the multiple selected microbe-related features may be a microbe belonging to the family Tannerellaceae of the genus Parabacteroides.

Comparative Example 1. Analysis Result of Feces Sample Treated with MCMOD and Feces Sample not Treated with MCMOD Feces were collected from one subject for 8 days, and 8 feces samples (J01, J02, J03, J04, J06, J08, J09 and J10) sorted by date were treated with MCMOD and then subjected to next-generation sequencing to analyze genes of microbes (Example). Similarly, feces samples not treated with MCMOD were subjected to next-generation sequencing to analyze genes of microbes (Comparative Example).

Figure 7A:
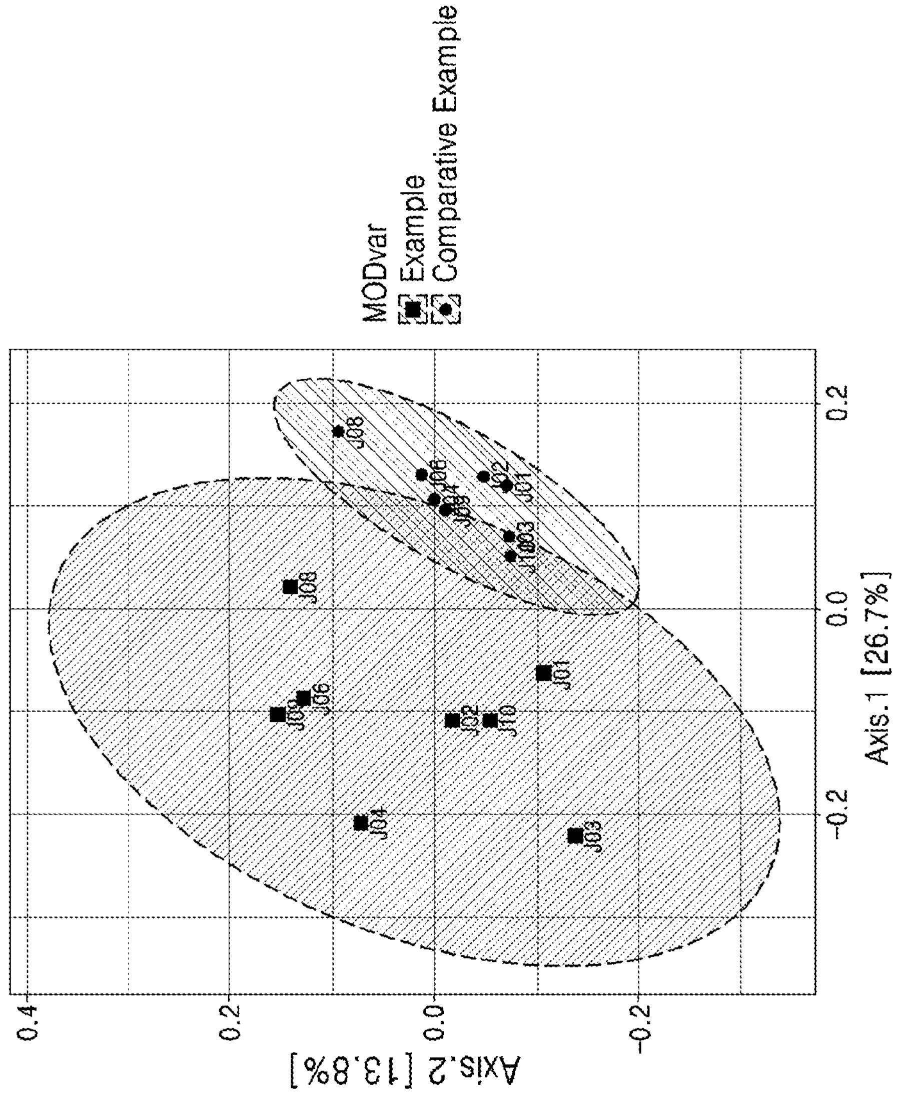
FIGS. 7A, 7B, and 7C are a diagram comparing analysis results of respective samples according to an enteric disorder determination method of an example of the present disclosure and a method of a comparative example.
Figure 7B:
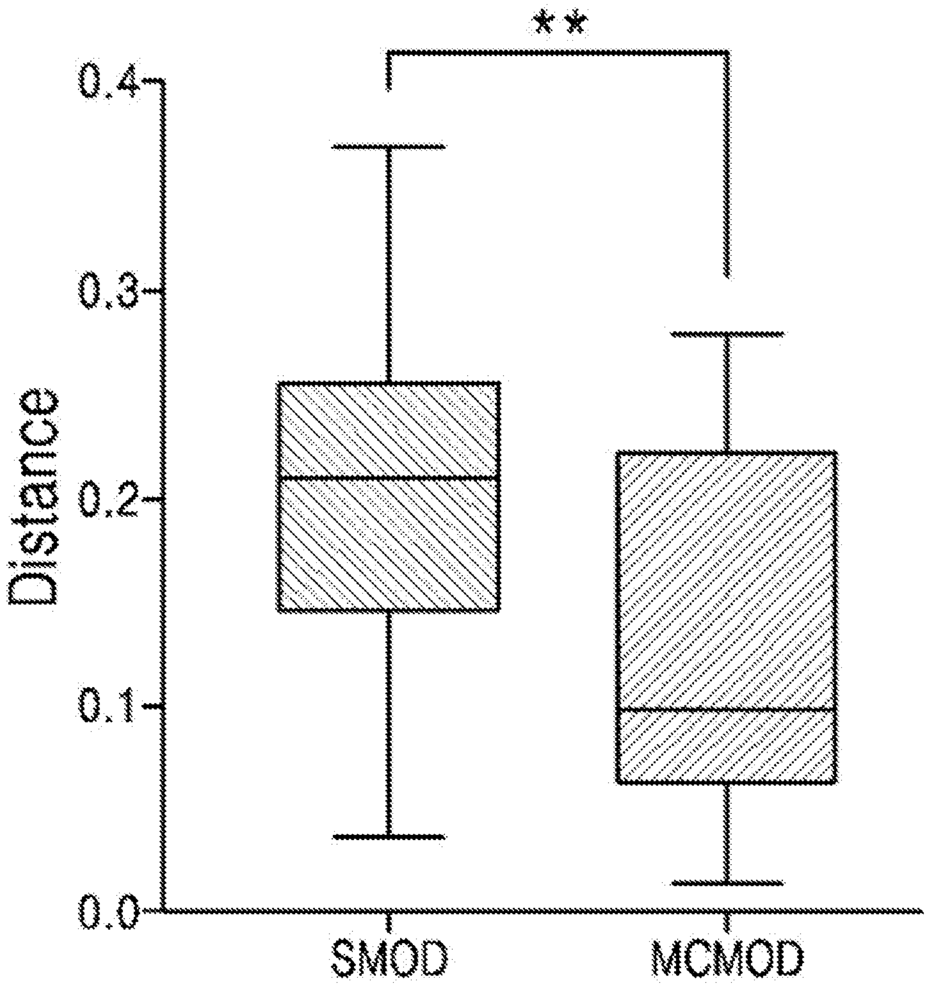
Figure 7C:
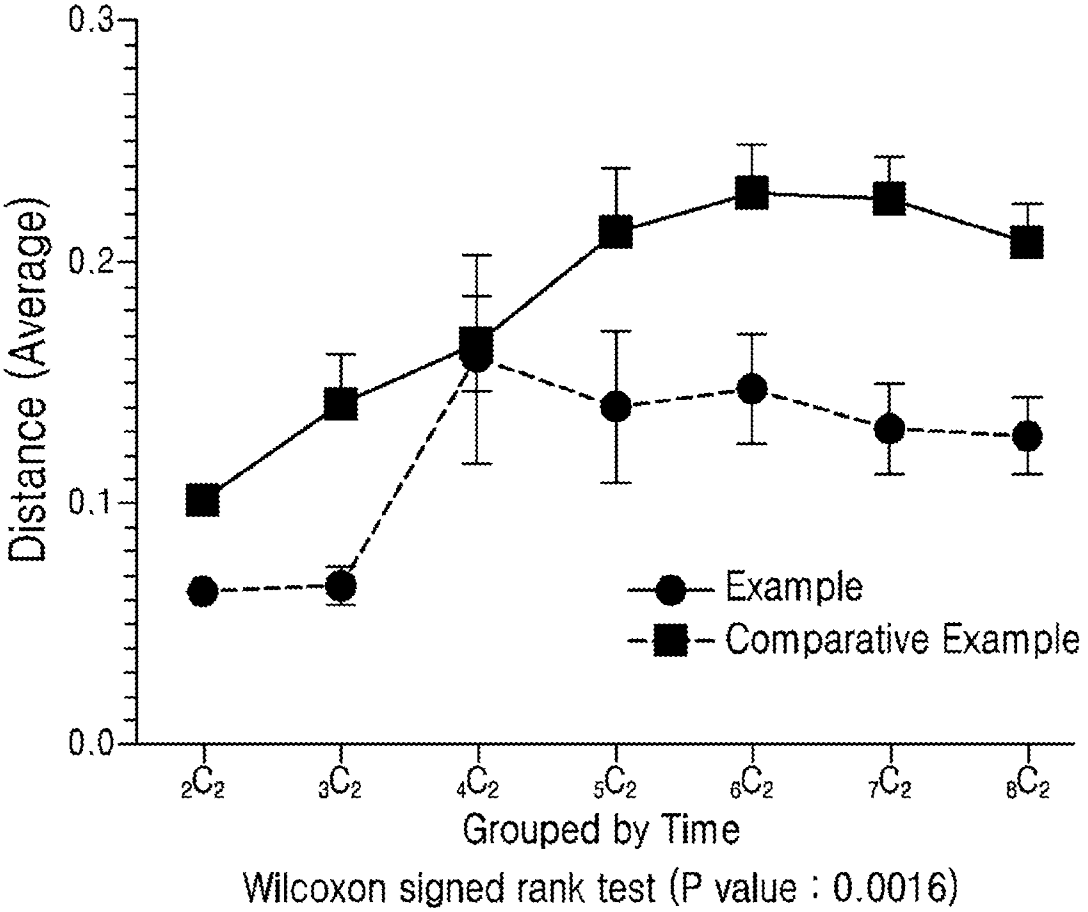
Figure 8A:
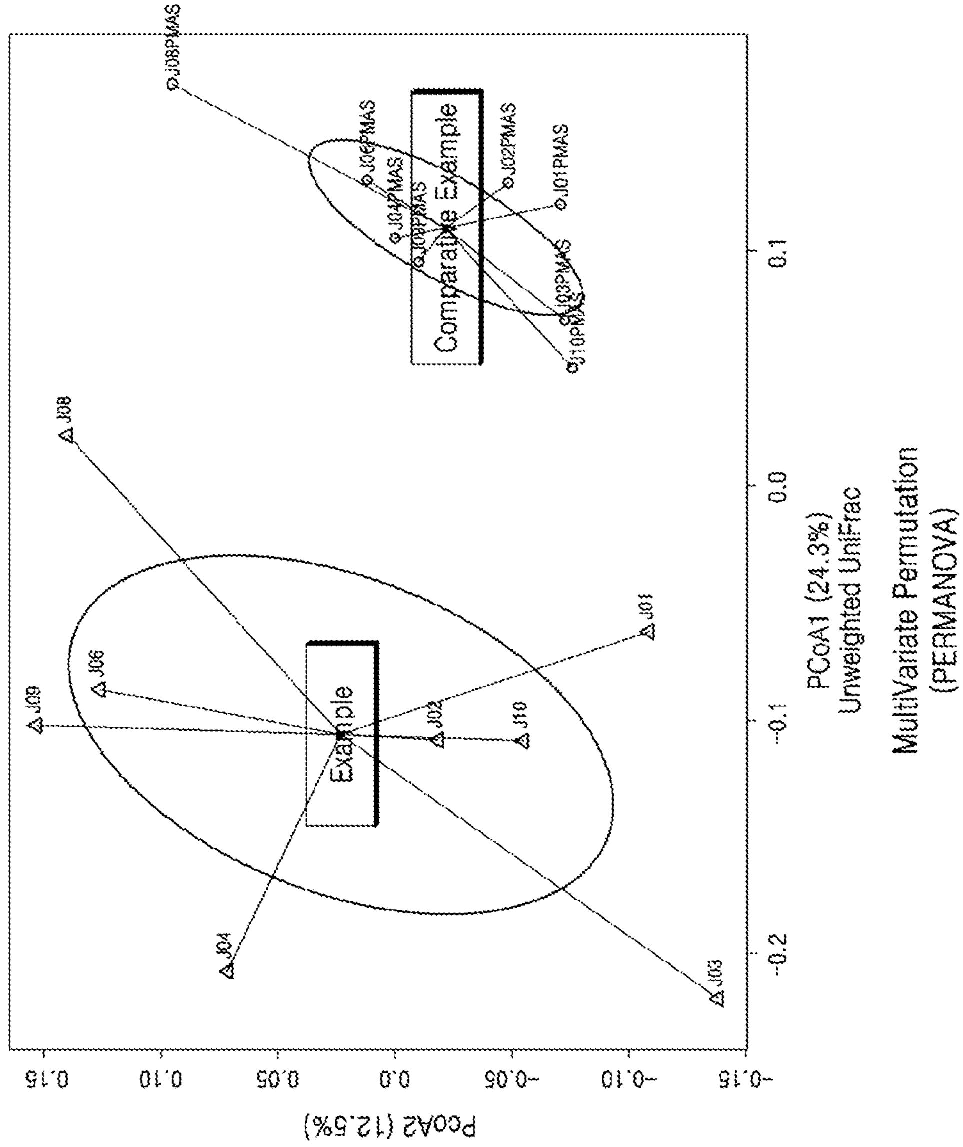

FIGS. 7A-7C are diagrams comparing analysis results of respective samples according to an enteric disorder determination method of Example of the present disclosure and a method of Comparative Example, FIGS. 8A-8B are diagrams comparing analysis results of respective samples according to an enteric disorder determination method of Example of the present disclosure and a method of Comparative Example.

FIG. 7A shows, as a PCoA plot, the beta diversity of the feces sample by using the Unweighted Unifrac Distance. As shown in the PCoA plot of FIG. 7A, it can be seen that the feces samples treated with MCMOD are relatively clustered, whereas the feces samples not treated with MCMOD are relatively scattered.

FIG. 7B shows, as a box plot, the distances among 8 points in each group (Example and Comparative Example) on the PCoA plot.

As can be seen from the box plot, the differences among the feces samples of Example are statistically significantly smaller than those of Comparative Example.

FIG. 7C shows the distances among 8 points in each group (Example and Comparative Example) on the PCoA plot.

Since there are 8 samples in each group, each group has a total of 28 types of distances between two samples. The samples with 28 types of distances were grouped in chronological order from 2C2 to 8C2.

Since a feces sample J01 was collected first and a feces sample J10 was collected last, the distance between the two samples collected first and second in the group 2C2 (N=1) (the distance between the samples J01 and J02) was calculated.

In the group 3C2 (N=3), the distances among the three samples including the next collected feces sample J03 (between J01 and J02, between J01 and J03, and between J02 and J03) were calculated to find the average and standard error of the distances.

In the group 4C2 (N=6), the distances among the four samples including the next collected feces sample J04 (between J01 and J02, between J01 and J03, between J01 and J04, between J02 and J03, between J02 and J04, and between J03 and J04) were calculated to find the average and standard error of the distances.

Similarly, in the group 8C2 (N=28), the distances among the eight samples including the last collected feces sample J10 (a total of 28 types of distances) were calculated to find the average and standard error of the distances.

As can be seen from the distance values in the PCoA plot, the differences among the feces sample groups (2C2 to 8C2) of Example are statistically significantly smaller than those of Comparative Example.

FIGS. 8A-8B show analysis results of the two groups (Example and Comparative Example) through PERMANOVA tests.

Based on the result of PERMANOVA tests as shown in FIGS. 8A-8B, a Pr(>F) value is as small as 0.001, which indicates that the two groups (Example and Comparative Example) are different in terms of population mean. This means there is a statistically significant difference between the two groups.

Also, it can be seen that the average distance to median of each feces sample in each group is smaller in Example (0.1792) than in Comparative Example (0.2340), which means that Example has less noise than Comparative Example.

As described above, the feces samples treated with MCMOD have relatively little noise due to a small bias between the feces samples and thus have low fluctuations.

That is, according to the present disclosure, the feces samples are treated with MCMOD before feature selection and machine learning training to facilitate feature selection, and, as will be described later, the machine learning model is trained to improve the performance of the machine learning model.

Comparative Example 2. Comparison of Performance of Machine Learning Models Trained Using Training Data Obtained from Feces Sample Treated with MCMOD and Feces Sample not Treated with MCMOD The feces samples collected in Example 1 were treated with MCMOD to extract microbial data (Example), and microbial data were extracted without MCMOD treatment (Comparative Example).

Specifically, as described above, after the primary selection was made from among a total of 978 features through the Boruta algorithm, the optimal number of features was set through the binomial deviance plot and multiple microbe-related features was selected through the XGB model.

By using the microbial data and microbe-related features of Example and Comparative Example, a LRA model, a random forest model, a GLM model, a gradient boosting model, and an XGB model were trained. Then, the performance of each machine learning model was evaluated.

Figure 9A:
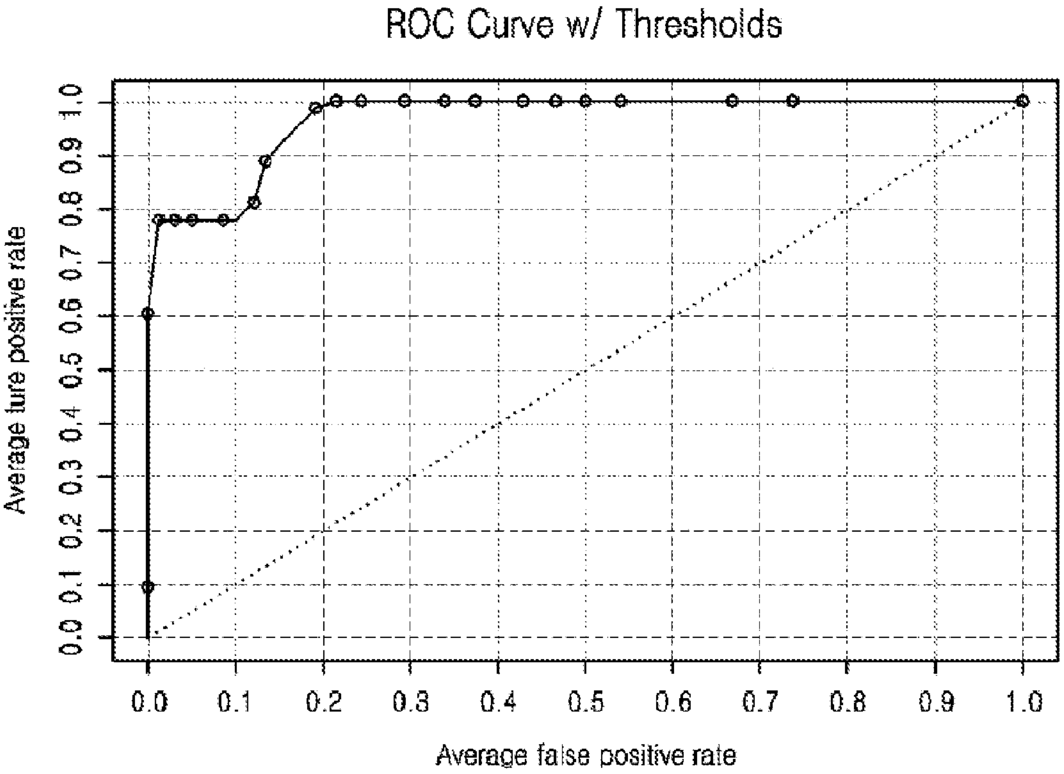
FIGS. 9A-9B show an ROC (receiver operating characteristic) curve and AUC (area under an ROC curve) scores for each of XGB models according to an enteric disorder determination method of an example of the present disclosure and a method of a comparative example.
Figure 9B:
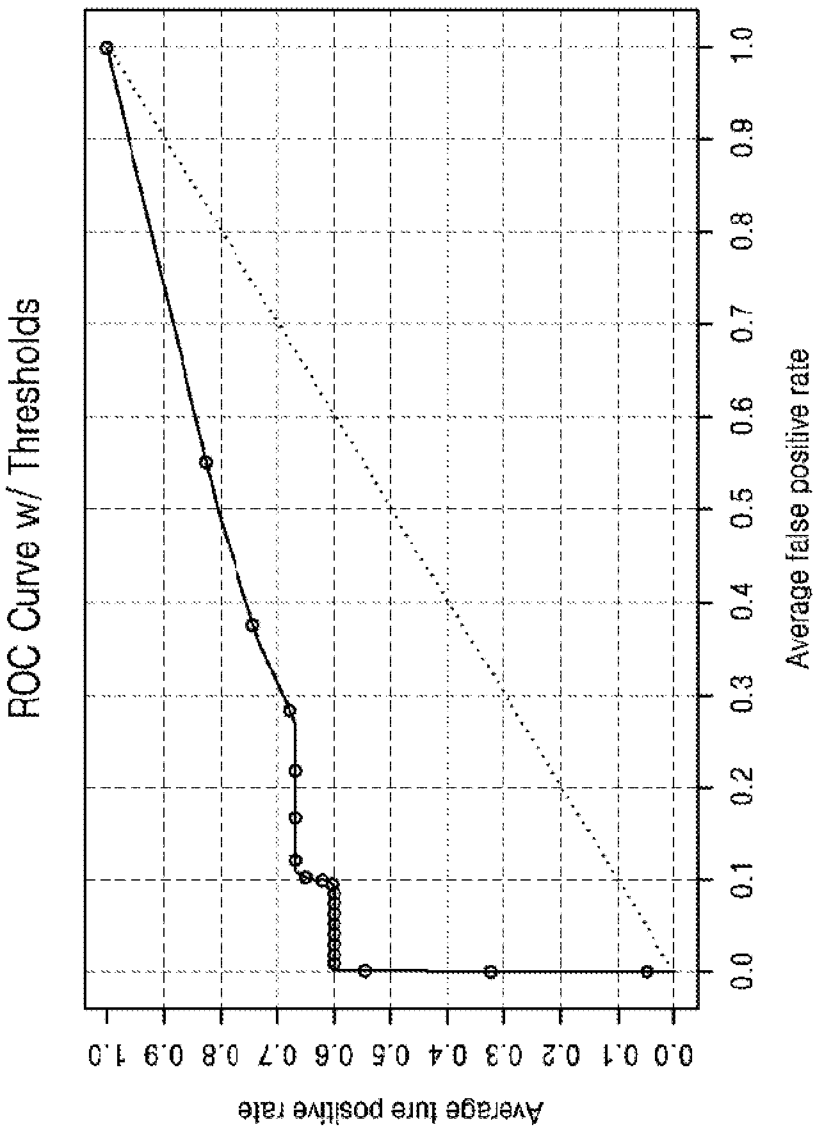

FIGS. 9A-9B show an ROC (receiver operating characteristic) curve and AUC (area under an ROC curve) scores for each of XGB models according to an enteric disorder determination method of Example of the present disclosure and a method of Comparative Example. FIGS. 10A-10B are diagrams comparing XGB models in terms of performance according to an enteric disorder determination method of Example of the present disclosure and a method of Comparative Example. Referring to FIGS. 9A-10B, the average true positive rate, the average false positive rate, the accuracy and the AUC values were higher in Example than in Comparative Example. Thus, it can be seen that when the microbial data of Example rather than Comparative Example were used, enteric disorder determination performance of the XGB model was enhanced.

Figure 11A:
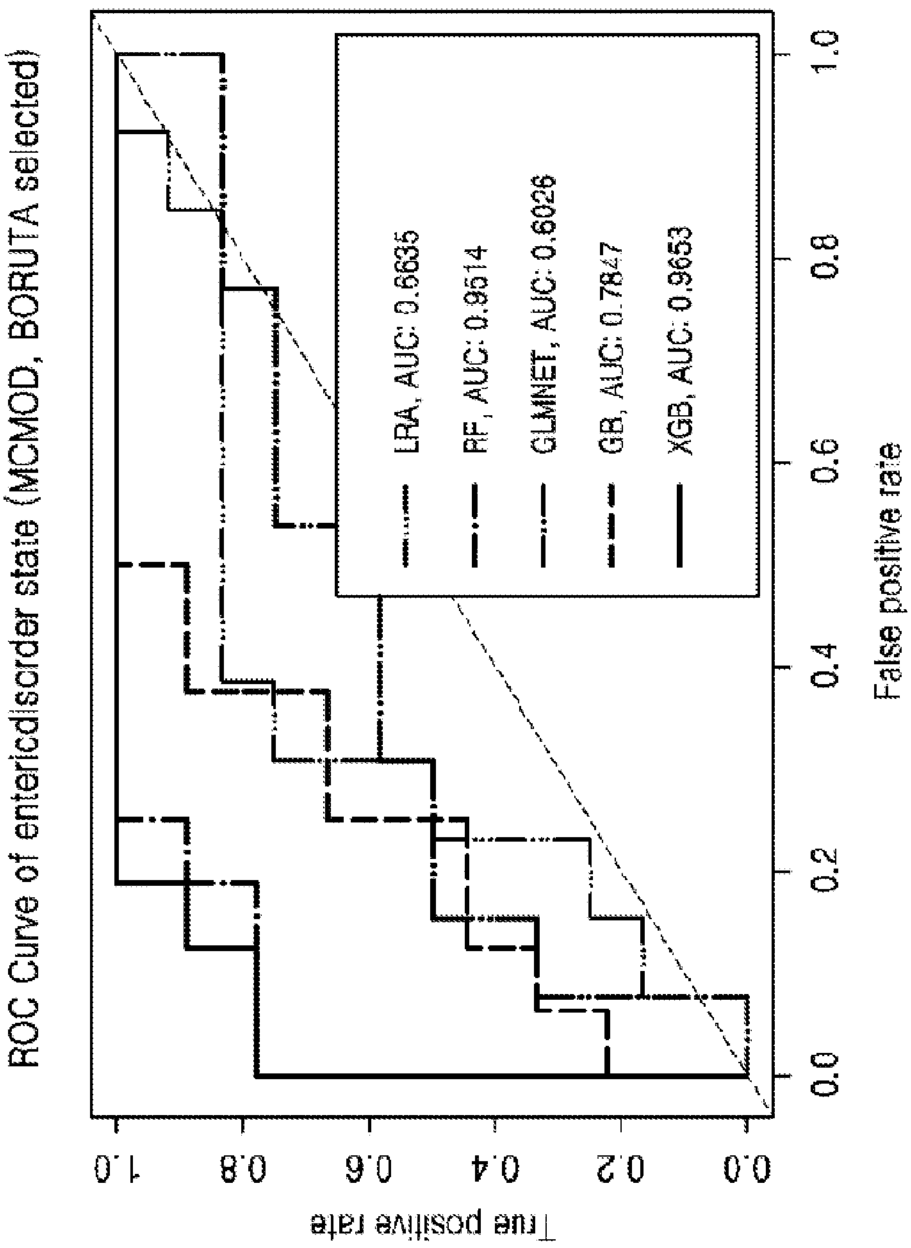
FIGS. 11A-11B are diagrams comparing machine learning models in terms of performance according to an enteric disorder determination method of an example of the present disclosure and a method of a comparative example.
Figure 11B:
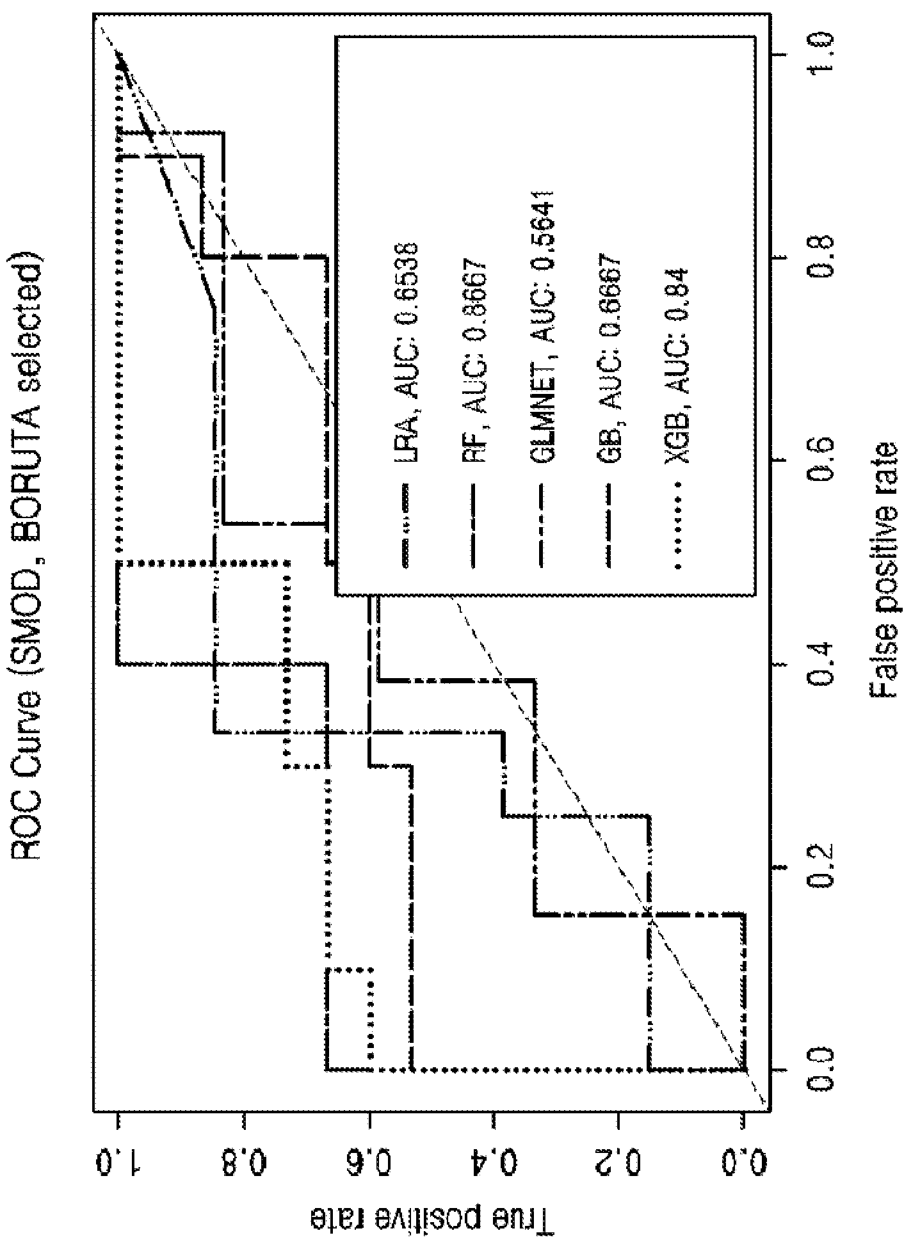

FIGS. 11A-11B are diagrams comparing machine learning models in terms of performance according to an enteric disorder determination method of Example of the present disclosure and a method of Comparative Example. As shown in FIGS. 11A-11B, it can be seen that when machine learning models were trained with the microbial data of Example, all the machine learning models of Example had higher performance than those of Comparative Example.

Figure 12A:
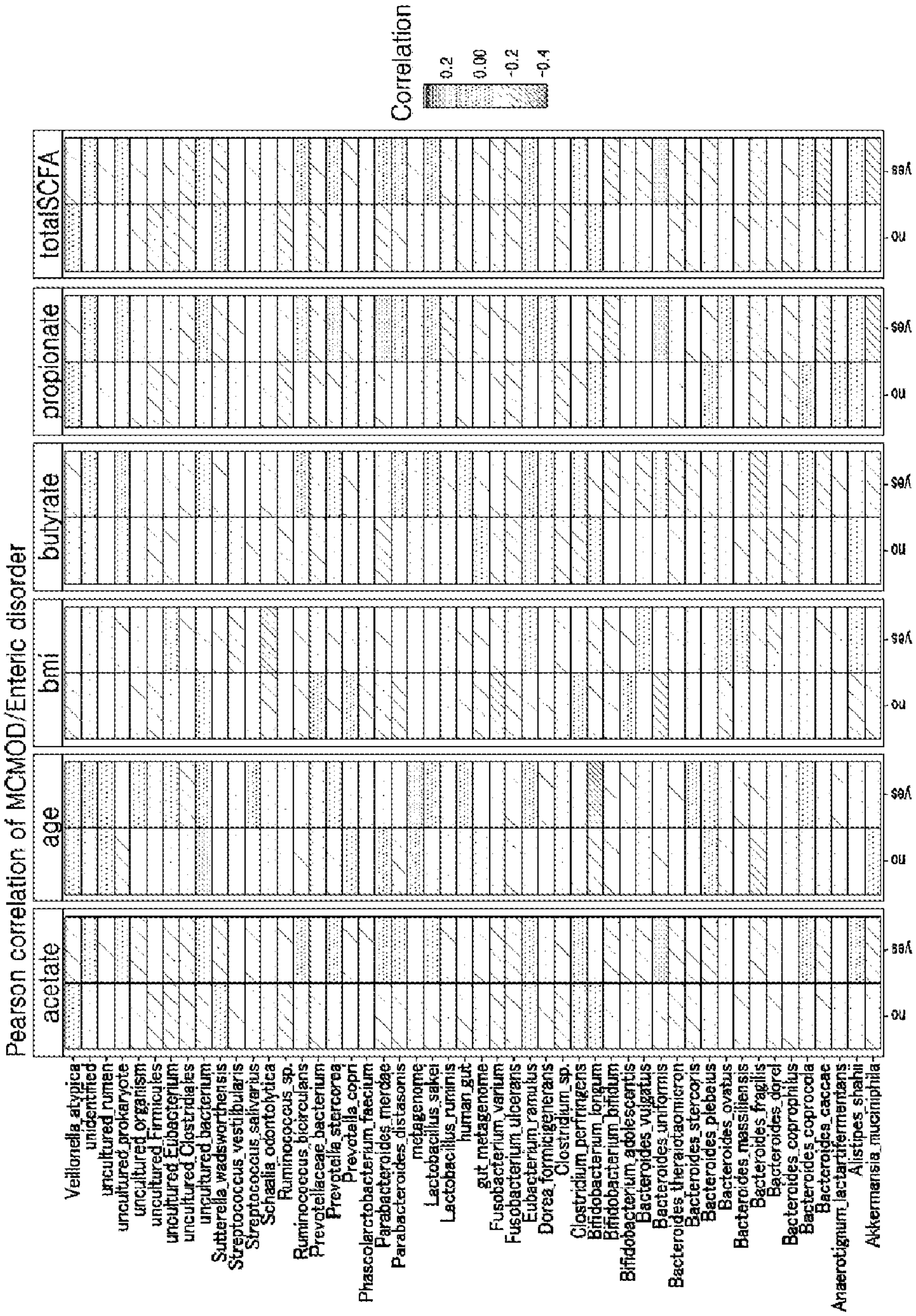
FIG. 12A is a diagram showing a Pearson's correlation with respect to a microbe distribution chart according to an enteric disorder determination method of an example of the present disclosure.
Figure 12B:
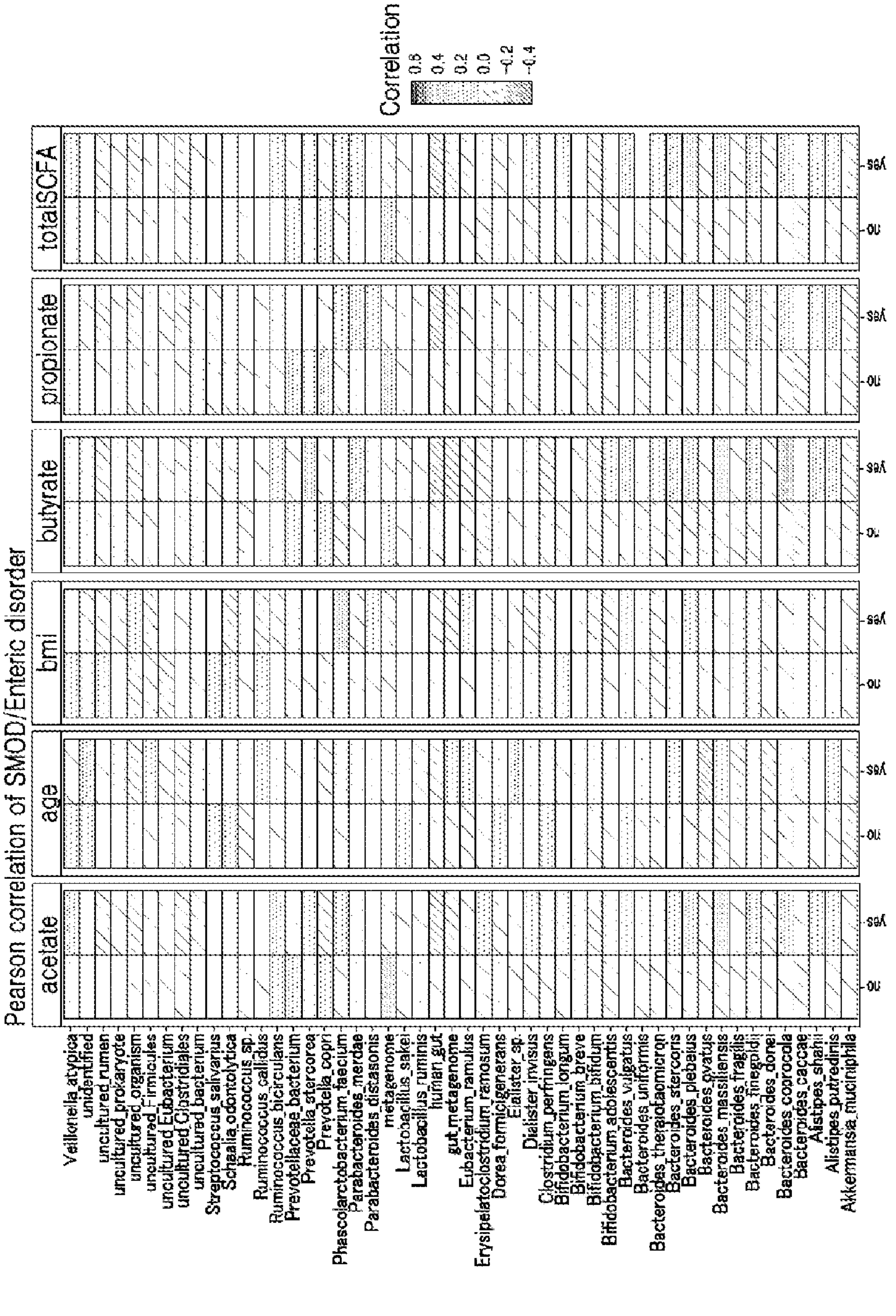
FIG. 12B is a diagram showing a Pearson's correlation with respect to a microbe distribution chart according to a method of a comparative example.
Figure 13A:
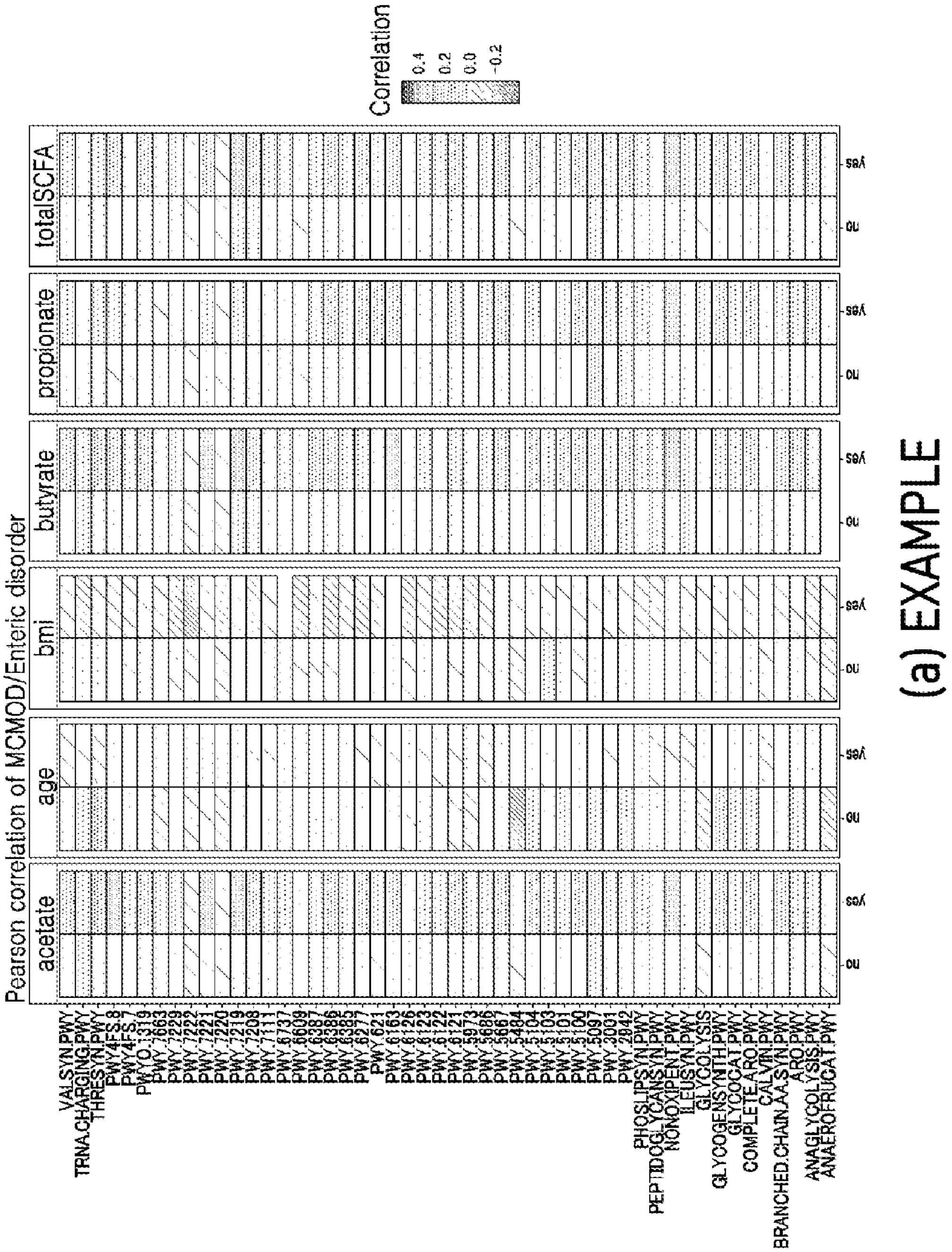
FIG. 13A is a diagram showing a Pearson's correlation with respect to each gene pathway prediction according to an enteric disorder determination method of an example of the present disclosure.
Figure 13B:
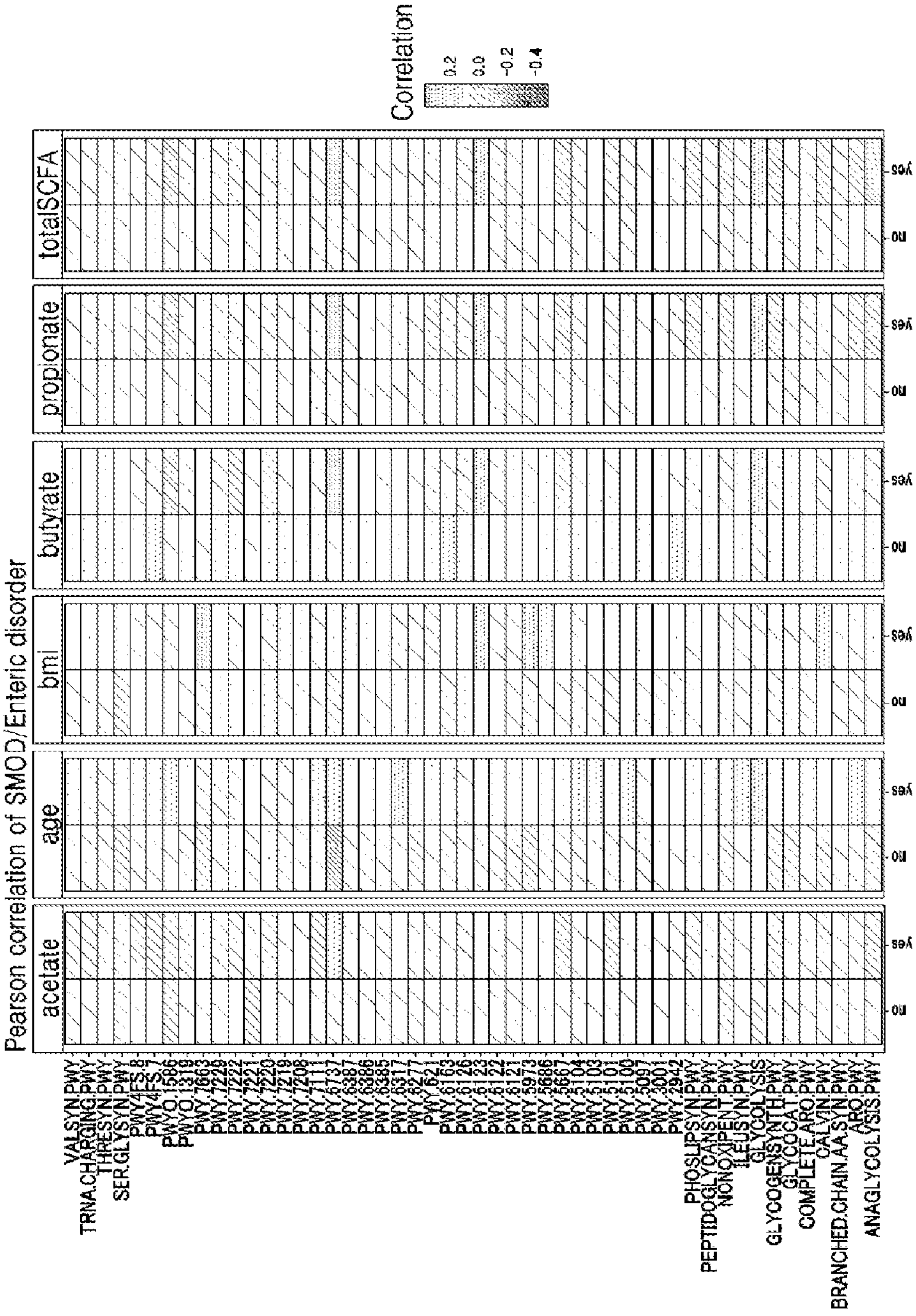
FIG. 13B is a diagram showing a Pearson's correlation with respect to each gene pathway prediction according to a method of a comparative example.

FIG. 12A is a diagram showing a Pearson's correlation with respect to a microbe distribution chart according to an enteric disorder determination method of Example of the present disclosure, and FIG. 12B is a diagram showing a Pearson's correlation with respect to a microbe distribution chart according to a method of Comparative Example. FIG. 13A is a diagram showing a Pearson's correlation with respect to each gene pathway prediction according to an enteric disorder determination method of Example of the present disclosure, and FIG. 13B is a diagram showing a Pearson's correlation with respect to each gene pathway prediction according to a method of Comparative Example. FIG. 12A and FIG. 12B compare Pearson's correlations among numerical data, such as microbial taxon abundance and age, body mass index (BMI), and acetate, propionate, butyrate and total short-chain fatty acid levels, of the data of Example and Comparative Example, and FIG. 13A and FIG. 13B compare Pearson's correlations between each gene pathway abundance and the above-described numerical data. Referring to FIG. 12A, FIG. 12B, FIG. 13A and FIG. 13B, the Pearson's correlation in the data of Example is higher than that of Comparative Example. Thus, it can be seen that the enteric disorder determination method according to Example is more useful than the enteric disorder determination method according to Comparative Example.

Figure 14A:
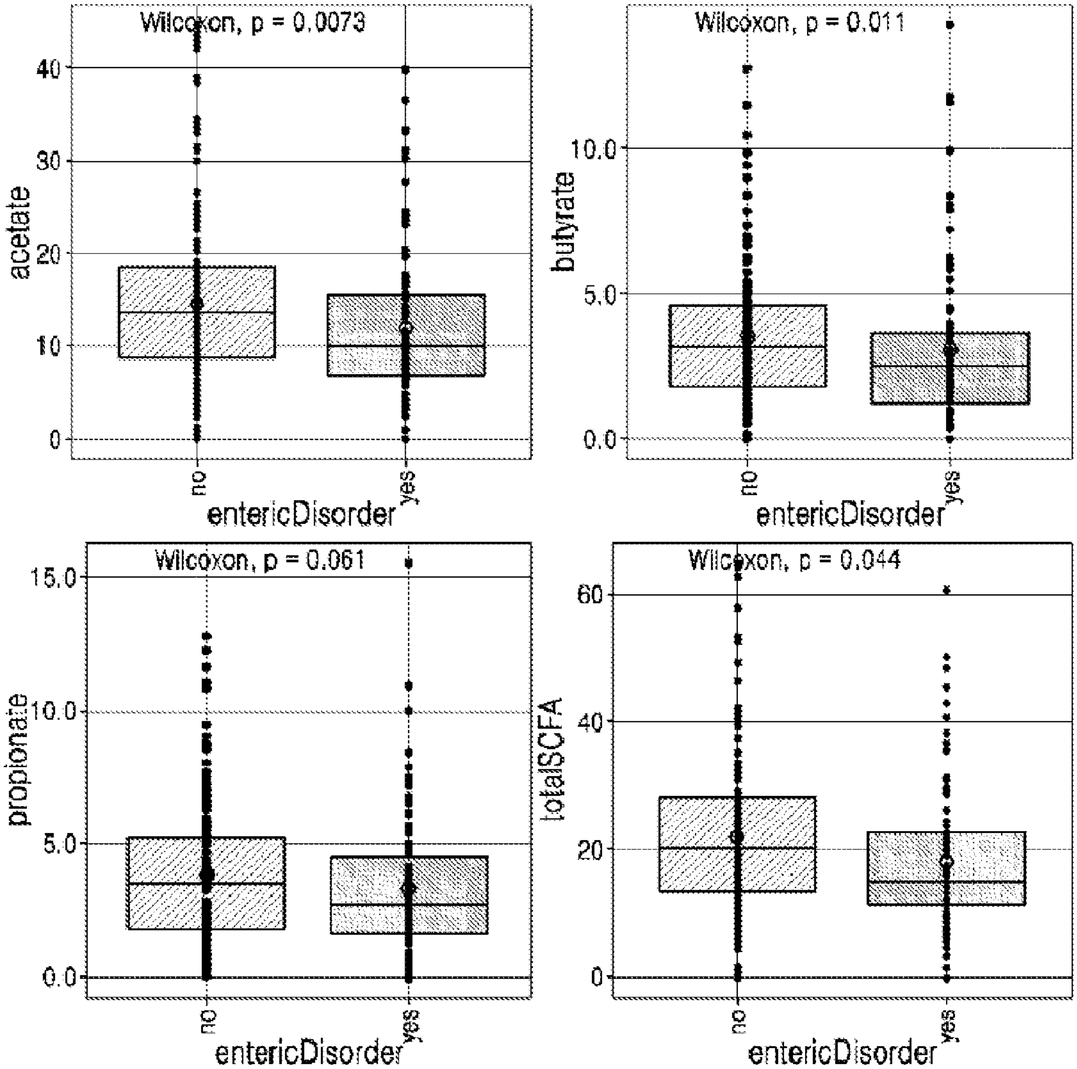
FIGS. 14A-14B are diagrams comparing the amounts of short-chain fatty acids (SCFAs) according to an enteric disorder determination method of an example of the present disclosure and a method of a comparative example.
Figure 14B:
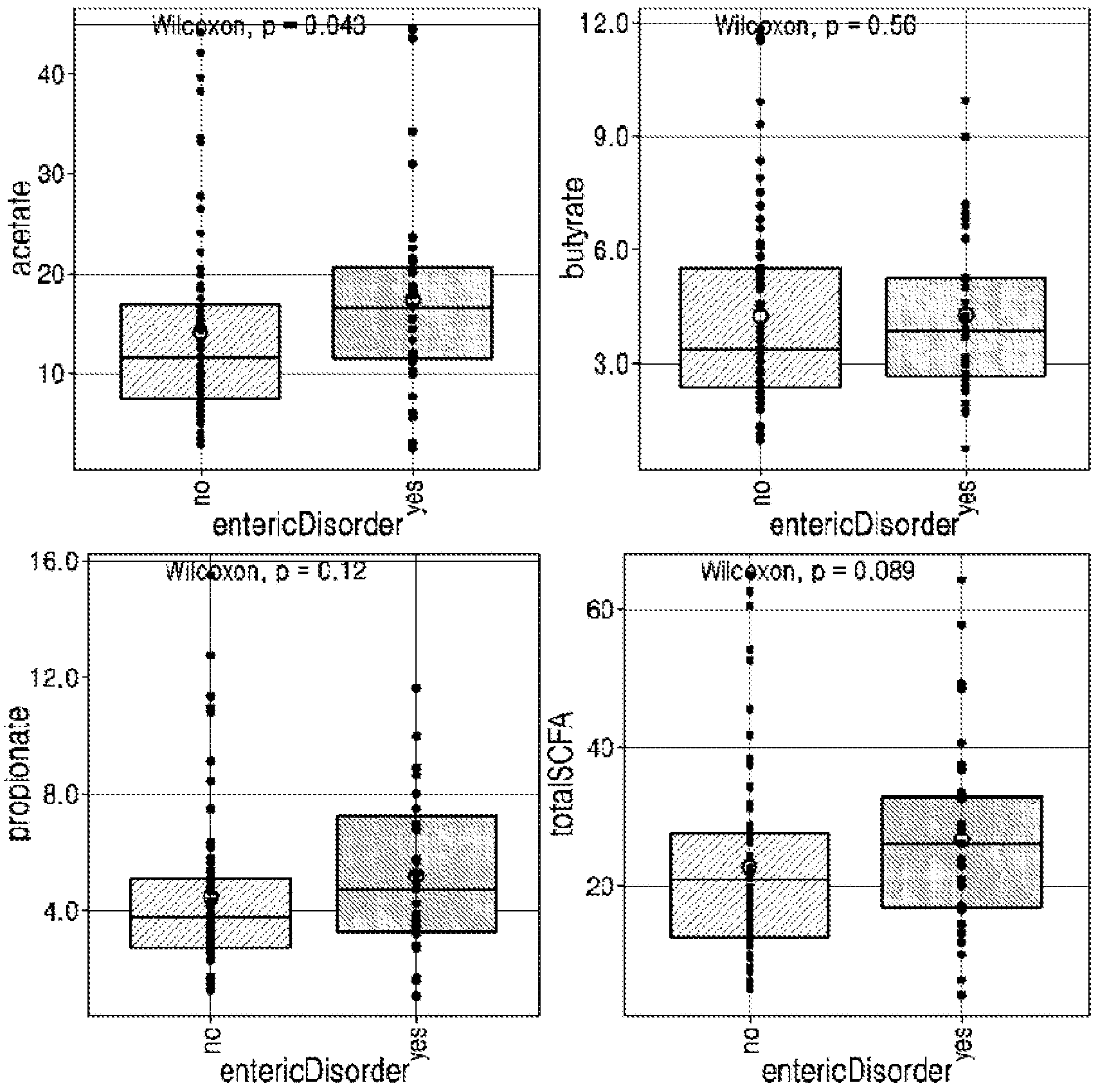

FIGS. 14A-14B are diagrams comparing the amounts of short-chain fatty acids (SCFAs) according to an enteric disorder determination method of Example of the present disclosure and a method of Comparative Example. In general, it is known that a greater absolute amount of SCFAs (acetate, propionate and butyrate) is more useful. It can be seen that the amounts of SCFAs are greater in the disease group than in the normal group according to Comparative Example, whereas the average is higher in the normal group according to Example or the difference decreases compared to Example even if the amounts of SCFAs are greater in the disease group. That is, it can be seen that an interpretation of the results was distorted by data noise in Comparative Example, whereas an interpretation of the results was more accurate in Example.

Figure 15:
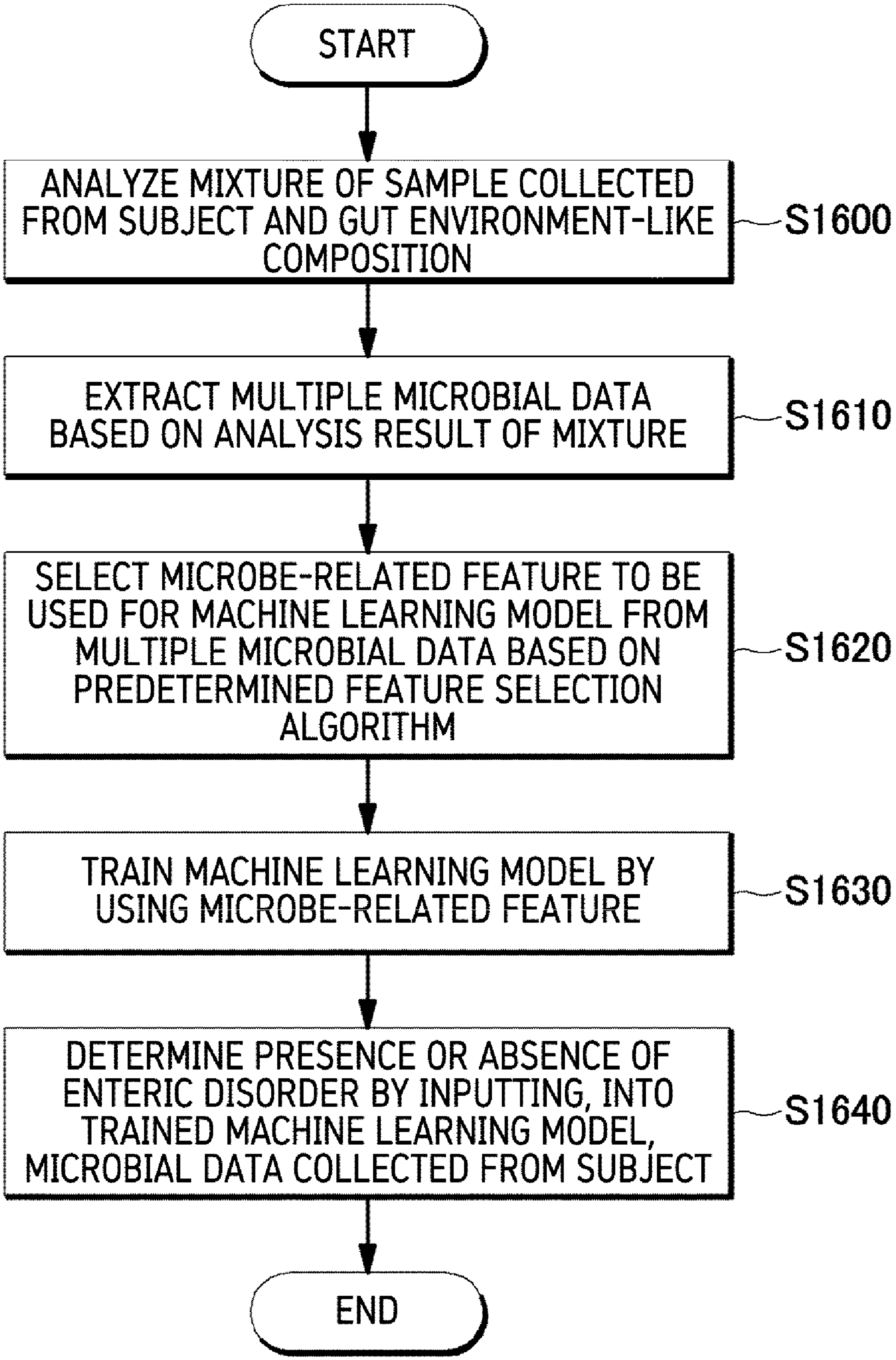
FIG. 15 is a flowchart showing a method for determining an enteric disorder according to an example of the present disclosure.

FIG. 15 is a flowchart showing a method for determining an enteric disorder according to an example of the present disclosure. The method for determining an enteric disorder according to the example illustrated in FIG. 15 includes the processes time-sequentially performed by the diagnostic apparatus illustrated in FIG. 1. Therefore, the above descriptions of the processes may also be applied to the method for determining an enteric disorder performed according to the example illustrated in FIG. 15, even though they are omitted hereinafter.

Referring to FIG. 15, a mixture of a sample collected from a subject and a gut environment-like composition may be analyzed in a process S1600.

In a process S1610, multiple microbial data may be extracted based on an analysis result of the mixture.

In a process S1620, a microbe-related feature to be used for a machine learning model may be selected from the multiple microbial data based on a predetermined feature selection algorithm.

In a process S1630, the machine learning model may be trained with the microbe-related feature.

In a process S1640, the machine learning model may be trained with the microbe-related feature.

The presence or absence of an enteric disorder can be determined by inputting, into the trained machine learning model, the microbial data collected from the subject to be tested.

The method for determining an enteric disorder illustrated in FIG. 15 can be embodied in a computer program stored in a medium or in a storage medium including instruction codes executable by a computer such as a program module executed by the computer. A computer-readable medium can be any usable medium which can be accessed by the computer and includes all volatile/non-volatile and removable/non-removable media. Further, the computer-readable medium may include all computer storage media. The computer storage media include all volatile/non-volatile and removable/non-removable media embodied by a certain method or technology for storing information such as a computer-readable instruction code, a data structure, a program module or other data.

The above description of the present disclosure is provided for the purpose of illustration, and it would be understood by a person with ordinary skill in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A method for determining an enteric disorder by using a machine learning model, comprising:

analyzing a mixture of a gut-derived substance collected from a subject and a gut environment-like composition, wherein the gut environment-like composition comprises L-cysteine hydrochloride and mucin;

extracting multiple microbial data based on an analysis result of the mixture, including culturing the mixture under anaerobic conditions for 18 to 24 hours, centrifuging the cultured mixture to separate a supernatant and a precipitate, and analyzing the supernatant and the precipitate to extract data on at least one of a content, a concentration or a kind of one or more of endotoxins, hydrogen sulfides, short-chain fatty acids (SCFAs) or microbiota-derived metabolites contained in the cultured mixture, and a change in kind, a concentration, a content or a diversity of bacteria included in the microbiota;

selecting multiple microbe-related features to be used for the machine learning model from the multiple microbial data based on a predetermined feature selection algorithm, wherein the selecting of the multiple microbe-related features comprises:

(a) performing a primary selection from features through a Boruta algorithm to select a subset of features;

(b) checking an error value depending on a number of features through a binomial deviance plot to determine an optimal range of the number of features, wherein the optimal range is 1 to 23;

(c) determining an optimal number of features within the optimal range based on accuracy, wherein the optimal number is 14; and (d) selecting the 14 multiple microbe-related features through an extreme gradient boosting (XGB) model based on importance of the features;

training the machine learning model by using the multiple microbe-related features, including performing supervised learning based on labeling of whether the enteric disorder is present for each of the microbial data and contents of microbes included in the selected multiple microbe-related features; and determining the enteric disorder by inputting, into the trained machine learning model, the microbial data collected from the subject to be tested, wherein the determining of the enteric disorder is based on an output value of the trained machine learning model, wherein each of the microbes is selected from genera comprising the family Tannerellaceae, the family Bifidobacteriaceae, the family Ruminococcaceae, the family Clostridaceae, the family Lachnospiraceae, the family Bacteroidaceae, the family Erysipelatoclostridiaceae, the family Veilonellaceae, the family Bacteroidaceae, the family Ruminococcaceae, the family Lachnospiraceae, and the family Anaerovoracaceae.

2. The method of claim 1, wherein each of the microbes is selected from species comprising the genus Parabacteroides, the genus *Bifidobacterium*, the genus Subdoligranulum, the genus *Clostridium*, the genus Ruminococcus, the genus *Bacteroides*, the genus Erysipelatoclostridium, the genus RF39, the genus *Veillonella*, the genus *Bacteroides*, the genus *Eubacterium*, the genus GCA.900066575, and the genus UCG.010.

3. A diagnostic apparatus for diagnosing an enteric disorder by using a machine learning model, comprising:

a processor; and a memory for storing instructions which when executed by the processor cause the processor to:

extract multiple microbial data based on an analysis result of a mixture of a gut-derived substance collected from a subject and a gut environment-like composition, wherein the gut environment-like composition comprises L-cysteine hydrochloride and mucin, including culturing the mixture under anaerobic conditions for 18 to 24 hours, centrifuging the cultured mixture to separate a supernatant and a precipitate, and analyzing the supernatant and the precipitate to extract data on at least one of a content, a concentration or a kind of one or more of endotoxins, hydrogen sulfides, short-chain fatty acids (SCFAs) or microbiota-derived metabolites contained in the cultured mixture, and a change in kind, a concentration, a content or a diversity of bacteria included in the microbiota;

select multiple microbe-related features to be used for the machine learning model from the multiple microbial data based on a predetermined feature selection algorithm, wherein the selecting of the multiple microbe-related features comprises:

(a) performing a primary selection from features through a Boruta algorithm to select a subset of features;

(b) checking an error value depending on a number of features through a binomial deviance plot to determine an optimal range of the number of features, wherein the optimal range is 1 to 23;

(c) determining an optimal number of features within the optimal range based on accuracy, wherein the optimal number is 14; and (d) selecting the 14 multiple microbe-related features through an extreme gradient boosting (XGB) model based on importance of the features;

train the machine learning model by using the multiple microbe-related features, and to perform supervised learning based on labeling of whether the enteric disorder is present for each of the microbial data and contents of microbes included in the selected multiple microbe-related features; and diagnose the enteric disorder by inputting, into the trained machine learning model, the microbial data collected from the subject to be tested, wherein diagnosing of the enteric disorder is based on an output value of the trained machine learning model, wherein each of the microbes is selected from genera comprising the family Tannerellaceae, the family Bifidobacteriaceae, the family Ruminococcaceae, the family Clostridaceae, the family Lachnospiraceae, the family Bacteroidaceae, the family Erysipelatoclostridiaceae, the family Veilonellaceae, the family Bacteroidaceae, the family Ruminococcaceae, the family Lachnospiraceae, and the family Anaerovoracaceae.

4. The diagnostic apparatus of claim 3, wherein each of the microbes is selected from species comprising the genus Parabacteroides, the genus *Bifidobacterium*, the genus Subdoligranulum, the genus *Clostridium*, the genus Ruminococcus, the genus *Bacteroides*, the genus Erysipelatoclostridium, the genus RF39, the genus *Veillonella*, the genus *Bacteroides*, the genus *Eubacterium*, the genus GCA.900066575, and the genus UCG.010.

* * * * *